United States Patent
Fritsch et al.

(10) Patent No.: US 7,650,194 B2
(45) Date of Patent: Jan. 19, 2010

(54) INTRACOCHLEAR NANOTECHNOLOGY AND PERFUSION HEARING AID DEVICE

(76) Inventors: Michael H. Fritsch, 6400 Old Cheney Rd., Lincoln, NE (US) 68516; John H. Fritsch, 6400 Old Cheney Rd., Lincoln, NE (US) 68516; Josephine Fritsch, 6400 Old Cheney Rd., Lincoln, NE (US) 68516

( * ) Notice: Subject to any disclaimer, the term of this patent is extended or adjusted under 35 U.S.C. 154(b) by 0 days.

(21) Appl. No.: 11/689,004

(22) Filed: Mar. 21, 2007

(65) Prior Publication Data
US 2007/0225776 A1 Sep. 27, 2007

Related U.S. Application Data

(60) Provisional application No. 60/784,885, filed on Mar. 22, 2006.

(51) Int. Cl.
*A61N 1/00* (2006.01)
(52) U.S. Cl. .................................................. 607/137
(58) Field of Classification Search ................. 607/137; 435/287.1; 600/372; 324/658; 604/891.1, 604/506; 977/700, 702; 606/129; 424/426
See application file for complete search history.

(56) References Cited

U.S. PATENT DOCUMENTS

| | | | |
|---|---|---|---|
| RE31,031 E | 9/1982 | Kissiah, Jr. | |
| 4,532,930 A | 8/1985 | Crosby et al. | |
| 4,617,913 A | 10/1986 | Eddington | |
| 4,819,647 A | 4/1989 | Byers et al. | |
| 4,832,051 A | 5/1989 | Jarvik et al. | |
| 4,892,108 A | 1/1990 | Miller et al. | |
| 5,123,422 A | 6/1992 | Charvin | |
| 5,653,742 A | 8/1997 | Parker et al. | |
| 5,674,264 A | 10/1997 | Carter et al. | |
| 5,755,747 A | 5/1998 | Daly et al. | |
| 6,112,124 A | 8/2000 | Loeb | |
| 6,151,526 A | 11/2000 | Tziviskos | |
| 6,205,360 B1 | 3/2001 | Carter et al. | |
| 6,301,505 B1 | 10/2001 | Money | |
| 6,374,143 B1 | 4/2002 | Berrang et al. | |

(Continued)

FOREIGN PATENT DOCUMENTS

EP 1574181 A1 9/2005

(Continued)

OTHER PUBLICATIONS

Cochlear Collaborative Research Report, "Research Toward an Endosteal Electrode Array", (Pau & Rodriguez) 2004.

(Continued)

*Primary Examiner*—George Manuel
(74) *Attorney, Agent, or Firm*—E. Victor Indiano; Indiano Vaughan LLP

(57) ABSTRACT

An intra-cochlear implant is provided for aiding in the hearing of a patient. The implant includes a body portion implantable within an interior of a cochlea of a patient. The body portion has a proximal end, a distal end and a primary axis. A plurality of signal carrying electrodes extends along the body portion. The electrodes have proximal ends and distal ends, with the proximal ends being capable of receiving a signal from a signal generator, and the distal ends being capable of delivering the received signal to an anatomical receptor within a cochlea. At least several of the plurality of electrodes have a nanoelectrode-sized portion. The implant also may include a fluid delivery system of tubules, reservoirs, and pumps for the delivery of chemicals and cells to activate regeneration of neural elements lost during the hearing loss process.

41 Claims, 11 Drawing Sheets

U.S. PATENT DOCUMENTS

| | | | |
|---|---|---|---|
| 6,408,855 B1 | 6/2002 | Berrang et al. | |
| 6,428,484 B1 | 8/2002 | Battner et al. | |
| 6,496,734 B1 | 12/2002 | Money | |
| 6,537,800 B1 * | 3/2003 | Karube et al. | 435/287.1 |
| 6,549,814 B1 | 4/2003 | Strutz et al. | |
| 6,556,870 B2 | 4/2003 | Zierhofer et al. | |
| 6,575,894 B2 | 6/2003 | Leysieffer et al. | |
| 6,636,768 B1 | 10/2003 | Harrison | |
| 6,648,914 B2 | 11/2003 | Berrang et al. | |
| 6,724,902 B1 | 4/2004 | Shennib et al. | |
| 6,946,851 B2 * | 9/2005 | Lee et al. | 324/658 |
| 7,044,942 B2 * | 5/2006 | Jolly et al. | 604/891.1 |
| 7,063,708 B2 * | 6/2006 | Gibson et al. | 606/129 |
| 7,146,227 B2 * | 12/2006 | Dadd et al. | 607/137 |
| 2001/0031974 A1 | 10/2001 | Hadlock et al. | |
| 2002/0029074 A1 | 3/2002 | Treaba et al. | |
| 2003/0045921 A1 | 3/2003 | Dadd et al. | |
| 2003/0097121 A1 | 5/2003 | Jolly et al. | |
| 2004/0115241 A1 * | 6/2004 | Calhoun et al. | 424/426 |
| 2004/0172118 A1 | 9/2004 | Gibson | |
| 2005/0015133 A1 | 1/2005 | Ibrahim et al. | |
| 2005/0080473 A1 | 4/2005 | Gibson et al. | |
| 2006/0264897 A1 * | 11/2006 | Lobl et al. | 604/506 |
| 2007/0060815 A1 * | 3/2007 | Martin et al. | 600/372 |

FOREIGN PATENT DOCUMENTS

| | | |
|---|---|---|
| WO | WO 2004/054474 A1 | 7/2004 |

OTHER PUBLICATIONS

Acta Otolaryngol (Stockh) 1988; 449: 55-57, Cochlear implant. Treatment of deaf people with cochlear implant—Reults of an 8-channel extracochlear implant.

Laryngoscope 113: May 2003; Development of a Novel Eighth-Nerve Intraneural Auditory Neuroprosthesis.

Acta Otolaryngol (Stockh) 1989; 107: 210-218; Development of Cochlear-wall Implants for Electrical Stimulation of the Auditory Nerve.

*The Journal of Laryngology and Otology*; Jun. 1985; vol. 99, pp. 549-553; Extracochlear eight-channel electrode system.

*Otolaryngologic Clinics of North America*; vol. 19, No. 2, May 1986; Extracochlear Sixteen-Channel Electrode System.

*The Laryngoscope*; 107: Aug. 1997; Implantation of the Lateral Cochlear Wall for Auditory Nerve Stimulation.

*The American Journal of Otology*; vol. 8, No. 3, May 1987; Titanium Implants in the Otic Capsule: Development of a New Multichannel Extracochlear Implant.

Part Two—The Human Ear; Fig. 72 (Date Unknown, Definitely Prior Art).

Allen M. Cassell, "Ultrasensitive Carbon Nano-Electrode Biosensor Technology", Center for Nanotechnology, University of California at Santa Cruz, Moffit Field, California, Apr. 22, 2004.

"Hearing with a Cochlear Implant", www.bionicear.com, Feb. 24, 2005.

"Hear Now and Always", www.Cochlear Americas.com.

"Med-EL Products Overview", www.medel.com, Feb. 24, 2005.

Badi, Arunkumar N., *Development of a Novel Eighth-Nerve Intraneural Auditory Neuroprosthesis*; Laryngoscope 113: May 2003.

* cited by examiner

INTRACOCHLEAR NANOTECHNOLOGY AND PERFUSION HEARING AID DEVICE

CLAIM OF PRIORITY

The instant application claims priority benefit to Michael Fritsch et al., U.S. Provisional Patent Application No. 60/784,885filed on 22 Mar. 2006, which disclosure is incorporated herein.

I. FIELD OF THE INVENTION

The present invention relates to hearing aid devices, and more particularly to an implantable intra-cochlear hearing aid device using nano-technology.

II. BACKGROUND OF INVENTION

The genesis of the instant invention was in the multiple deficiencies that the Applicants found with existing intra-cochlear hearing aid implants of the ear. To understand the issues that give rise to the need for implantable hearing aids, it is helpful to first understand the anatomy and physiology of the ear, and in particular, the cochlea and its associated structures.

Referring to FIG. 3, there is shown a sectional view of the anatomy of the human auditory system A. At a macro level, the human auditory system A consists of the outer ear 0, the middle ear M, and the inner ear I. The outer ear 0 includes the pinna or auricle 21 and the ear canal 25 that provides communication from the outer ear 0 to the middle ear M. The middle ear M includes the eardrum (tympanic membrane) 10, the ossicles 17 consisting of the hammer (malleus bone) 24, the anvil (incus bone) 19, and the stirrup (stapes bone) 20, with the stapes tendon 11 providing support for the ossicles 17, and the eustachian tube 26. The middle ear M also includes the oval window 12 to which is attached the stirrup 20 for communication there through and the round window 18 which provides communication with the scala tympani ST.

The inner ear has two main components which are the semi-circular canals 22 and the cochlea 30. The endosteum 9 lines the entire inner surface of the inner ear I. The cochlea 30 includes the scala tympani ST, the scala media SM and the scala vestibuli SV. The perilymphatic chamber of the vestibular system has a wide connection to scala vestibuli SV, which in turn connects to scala tympani 14 by an opening called the helicotrema 16 at the apex of the cochlea 30. The scala tympani ST is then connected to the cerebrospinal fluid of the subarachnoid space by the cochlear aqueduct. The cochlear nerve AN sometimes referred to as Auditory Nerve AN extends from the cochlea 30 to the brain.

The reader's attention is directed to FIGS. 1 and 1A, which illustrate the cochlea. As a background, the Organ of Corti is denoted by "OC" in FIGS. 1 and 1A. (FIGS. 1 and 1A were taken from www.hoorzaken.nl/de_cochlea.htm and www-.wikipedia.org.).

The cochlea is a spiraled, hollow conical chamber of bone. Its structures include the scala vestibuli SV which contains perilymph and lies superior to the cochlear duct and abuts the oval window. The scala tympani ST contains perilymph, and lies inferior to the scala media and terminates at the round window. The scala media SM contains endolymph, and is the membraneous cochlear duct containing the Organ of Corti OC. The helicotrema is the location where scala tympani ST and the scala vestibuli SV merge. The Reissner's membrane RM separates the scala vestibuli SV from the scala media SM. The basilar membrane BM separates the scala media SM from the scala tympani ST.

The Organ of Corti OC is the peripheral end-point of the hearing nerves and contains hair cells and other cellular anatomy. The Organ of Corti is where the mechanical energy of sound waves is transformed into the electrical energy of nerve impulses. The Organ of Corti transforms mechanical sound energy into electrical stimuli which the ganglion cells carry to the cochlear nerve (also known as the Auditory Nerve AN) and then to the brain. In a deaf person, the Organ of Corti is either non-functional or is missing. In many deafness pathologies, the cochlear duct, which is the fluid space that contains the Organ of Corti, becomes devoid of functioning anatomy, and it is basically a non-functional fluid space. Even though the ear bones are vibrating and the inner ear fluids are vibrating, if the Organ of Corti is not functioning, then mechanical energy cannot be turned into electrical energy.

In some respects, the Organ of Corti operates much like a microphone head in that it picks up the sound wave energy and converts it to electrical energy. The nerves from the Organ of Corti travel along the osseous spiral lamina back to the spiral ganglion and from there, they continue by way of the cochlear nerve into the brain. In a hearing impaired person, the anatomy within the cochlear duct is often destroyed. In other words, the Organ of Corti does not function since there are no anatomical parts to perform any functions. It is analogous to having the head of the microphone cut off or destroyed.

When the Organ of Corti is functionally dead, nerves degenerate along the osseous spiral lamina and back to the spiral ganglion. One can look at the spiral ganglion as the wire that feeds the microphone and which terminates at the microphone head or Organ of Corti. Aiding the non-functional ear by using a hearing device known as a cochlear implant substitutes an electronic device for the Organ of Corti. The electrical device directly electrically stimulates the remaining nerve elements with an electrical pulse analogous to the function of the Organ of Corti. Because one no longer has the microphone head-like Organ of Corti to transduce mechanical sound energy to an electrical signal energy. What one is doing by employing a cochlear implant is delivering electrical impulses directly into the "wire of the microphone" or in this case, the spiral ganglion.

If any of these structures are damaged, normal function of the overall hearing mechanism is decreased. Further, when medical care of hearing loss is rendered, specifically with cochlear implantation, if the anatomic structures, in addition to the Organ of Corti, are decreased in number or not present to transmit the stimulus provided by the implant, a poor result would be expected from the cochlear implant. Thus, maximal presence of the internal anatomy of the cochlea and its related structures is paramount in restoring hearing through the use of a cochlear implant.

Prior art intra-cochlear implants exist, and were first seen in the late 1950s and early 1960s. A typical prior art intra-cochlear implant 99 is shown schematically in FIG. 2. Other examples of prior art intra-cochlear implants are shown in the patents cited in the application file. When cochlear implants were first being conceived and tested, it was not known how best to approach the cochlear nerve with the electrical impulse electrode studs. Some people felt that it was preferable to provide an intra-cochlear implant that was placed within the scala tympani or scala vestibuli, whereas others believed it preferable to employ an extra-cochlear implant that was placed exteriorly of the scala tympani and scala vestibuli. The extra-cochlear electrodes, which are not the subject at hand, at that time were basically placed on the unaltered or minimally altered bone of the cochlea and then secured to the bone. An improved extra-cochlear implant is shown in Fritsch et al., co-pending U.S. patent application Ser. No. 11/451,715 filed 13 Jun. 2006.

Intra-cochlear implants, of the types that this patent application addresses have to transmit electrical signals through the cochlear fluids of the scala vestibuli or scala tympani and the bone of the modiolus to reach the residual dendrites and spiral ganglia nerve cells.

One of the problems in dealing with intra-cochlear implants is that the small size of the inner ear structures such as the Organ of Corti, dendrites, spiral ganglion cells, and all the other anatomic structures within the cochlea severely limits the size of any intra-cochlea implant.

Returning to FIGS. 1,1A and 2, the usual intra-cochlear implant is preferably placed within the scala tympani ST of the cochlea although it can also be placed in the scala vestibuli SV. However, as the implant is relatively large and stiff, as it coils through the cochlea, the implant can act like a bulldozer that may penetrate through, rip and even strip out the other membranes and the lining endosteum, including everything from dendrites, osseous spiral lamina, vestibular ligament, spiral ligament, basilar membrane BM, stria vasularis, and to the Corti's organ OC of hearing. Such implant-induced damage deleteriously impacts the performance of the spiral ganglion SG and the cochlear nerve AN that are in the modiolus. The spiral ganglion SG is an important structure because this is where residual nerve cells in sensory hearing loss reside and are those that initiate transmission of the implant's electrical impulse to the cochlear nerve AN and eventually to the brain. Thus, an intra-cochlear implantation technique can be very traumatic and reduce the ability of the implant to successfully stimulate residual neural elements in patients with hearing loss. FIG. 2 diagrammatically shows the prior art implant electrode wire 100 of an intra-cochlear implant attached to the electrode 102 with stimulating points 103 within the cochlea.

Over time, technology has progressed, and improvements have been made in intra-cochlear implants. Currently, there exist three major manufacturers of intra-cochlear implanted hearing aid devices, including Cochlear Corporation (Melbourne, Australia); Med-El Corporation (Innsbruck, Austria); and Advance Bionics, which is now a unit of Boston Scientific Co. (Natick, Mass., USA).

Some implants now manufactured are slimmer, more flexible and designed to help overcome the initial problems of stiffness which caused great degrees of trauma. There may be lesser degrees of trauma with these newer implants although the damage they can potentially cause is still considerable. A typical implant will go into the cochlea up to about 20-30 mm, although some of them only go in up to 6 mm. The cochlea measures about 36 mm. in length. FIGS. 2 and 3 show a basic schematic of an intra-cochlear implant position and some ear macro-anatomy. It should be noted that with increasing loss of function and degeneration of the Organ of Corti, there is a serial degeneration seen in the dendrites and spiral ganglion cells. Thus, even without cochlear implant insertion trauma, suboptimal numbers of dendrites and spiral ganglion cells will be present. Indeed, there is a direct correlation between hearing loss within the audiometric spectrum and loss of anatomic structure. Implant insertion trauma further adds to the degeneration and loss of neural elements such as the dentrites and spiral ganglion cells.

Another major problem with present implants is that they have a relatively limited number of electrodes from which to stimulate the cochlea. Intra-cochlear implants known currently to Applicants range from one to 24 mono or bipolar electrodes. The number of original cells within the human Organs of Corti that stimulate the spiral ganglion cells and cochlear nerve are in the tens of thousands (~30,000). Thus, a major deficiency of present implants is that they do not adequately stimulate in numbers all along the cochlea. The result is lack of resolution within the sound-perception spectrum. Each single electrode substitutes for thousands of originally functioning cells.

Another major problem with presently available implants is that they do nothing to help regenerate any of the anatomic deficiencies just described. With present implants there are no means of delivering chemicals, medications, nutrients, nucleotides, and cells into the cochlea and/or perfusion of these substances and cells into and out of the cochlea.

Another deficiency with presently available implants is that electrical stimulus transmission is not transmitted from an electrode stud to a nerve structure by directly touching or even being intimate to one. Presently manufactured implants have intra-cochlear electrodes that must traverse fluid and bone to reach residual nerve tissue elements. Compared to directly touching nerve elements, it takes an extraordinary amount of electrical stimulation energy to appropriately stimulate the spiral ganglia and nerve cells through fluid and bone. Also, there is dispersion of the electrical energy from the electrode stud that causes the electrical signals to impact a wide area, and hence a large number of ganglia, as opposed to a small specific point on the cochlea. Additionally, the farther away the electrode studs are from the nerve elements, the more electrical power is required and used.

The cochlea is organized "tonotopically". In other words, specific tone frequencies are found at specific points along the length of the cochlea. At the cochlear basal turn, the cochlear duct membranes and their adjacent ganglion and nerve cells are where those ganglia and receptors are positioned that are designed for being receptive to high frequencies and at the very apex, the cochlear duct areas are where those ganglia are positioned that are receptive to the lowest frequencies are located. Thus, when one inserts a cochlear implant close to the round window in the usual cochleostomy procedure, the implant first will advance past the cochlear parts that stimulate high frequencies, then advance through the mid-frequencies and then to the lower frequencies.

Because of the tonotopic anatomy, if one puts a broadly dispersed electrical stimulus impulse into the cochlea, the impulse will impact spiral ganglion cells that cover a wide tonotopic range, and will not be as tonally specific. Rather than sampling a very narrow frequency spectrum of the tonotopic arrangement the impulse would then stimulate a very wide swath of frequencies.

Therefore, a major deficiency of the intra-cochlear implant prior art is the relatively low number of stimulating electrode points that are placeable on an implant. If one has a greater number of electrode studs, then one has more electrode spots on the implant with which to stimulate more individual nerve elements. Increasing the number of stimulated spots in the cochlea has the potential to result in more frequency differentiation and sound understanding which would likely result in a more accurate auditory experience for the user. Also, the more closely the stimulating electrode studs are positioned to the residual ganglion nerve cells, the more likely that the electrical signal output of the studs are to be focused on the ganglion cells of interest for that particular tone. Conversely, the greater the distance between stud and targeted ganglia, the more likely the stimuli will get dispersed and not impact the ganglion cells of interest, but rather impact ganglion cells over a wide tonal section.

The internal cochlear implants that exist now serve their intended function to a limited extent. However, room for improvement exists to provide an intra-cochlear implant that overcomes one or more of the preliminary deficiencies of current, known implants. As alluded to above, the primary drawbacks of current known implants are: (1) the internal destruction they cause to the cochlea; (2) the size limitations that they impose; (3) the lack of tonal and tonotopic specificity; (4) the lack of direct nerve touching electrical stimulation; and (5) the lack of a mechanism to achieve anatomic regeneration. One of the vexing problems that face those designing implants is the limitations that exist on the potential size of implant. Implant size limitations exist because there is only so much internal diameter to the cochlea to allow an electrode to pass. Thus, current technology only allows for so many electrode stimulating studs inside the cochlea because the sum diameter of the many numbers of wires to the electrode studs is limited by the cochlear diameter. The electrode sizes are destructively large and stiff. Additionally, the space limitations do not allow for perfusion hardware and cell-nerve regeneration techniques within the cochlea.

One object of the present invention is to provide an intra-cochlear implant that overcomes or at least reduces the severity of one or more of the deficiencies described above, of prior art intra-cochlear implants.

III. SUMMARY OF THE INVENTION

In accordance with the present invention, an intra-cochlear implant is provided for aiding in the hearing of a patient. The implant includes a body portion implantable within an interior of a cochlea of a patient. The body portion has a proximal end, a distal end and a primary axis. A plurality of signal carrying electrodes extends along the body portion. The electrodes have proximal ends and distal ends, with the proximal ends being capable of receiving a signal from a signal generator, and the distal ends being capable of delivering the received signal to an anatomical receptor within a cochlea. At least several of the plurality of electrodes include a nanoelectrode-sized portion.

Preferably, the body portion comprises a bundle containing a plurality of electrodes, wherein the electrodes have different lengths, so that the distal ends of the various electrodes may be placed at various axial positions along the length of the interior of the cochlea to thereby stimulate various tonotopic regions of the cochlea.

In accordance with another embodiment of the present invention, an intra-cochlear implant is provided for aiding in the hearing of a patient. The implant comprises a body portion implantable within an interior of a cochlea of a patient. A plurality of signal-carrying electrodes exist that are capable of receiving a signal from a signal generator and delivering the received signal to an anatomical receptor within a cochlea. The implant also includes a fluid delivery tubule having a proximal end and a distal end. The proximal end is capable of receiving a fluid from a fluid source. The tubule includes a distal end that is disposed within an interior of the cochlea, and is capable of delivering received fluid to the interior of the cochlea.

The present invention will be understood in more detail from the drawings and description presented below, that described the best mode perceived presently by the applicants of practicing the present invention.

IV. BRIEF DESCRIPTION OF DRAWINGS

IV. DETAILED DESCRIPTION

Figure 1:
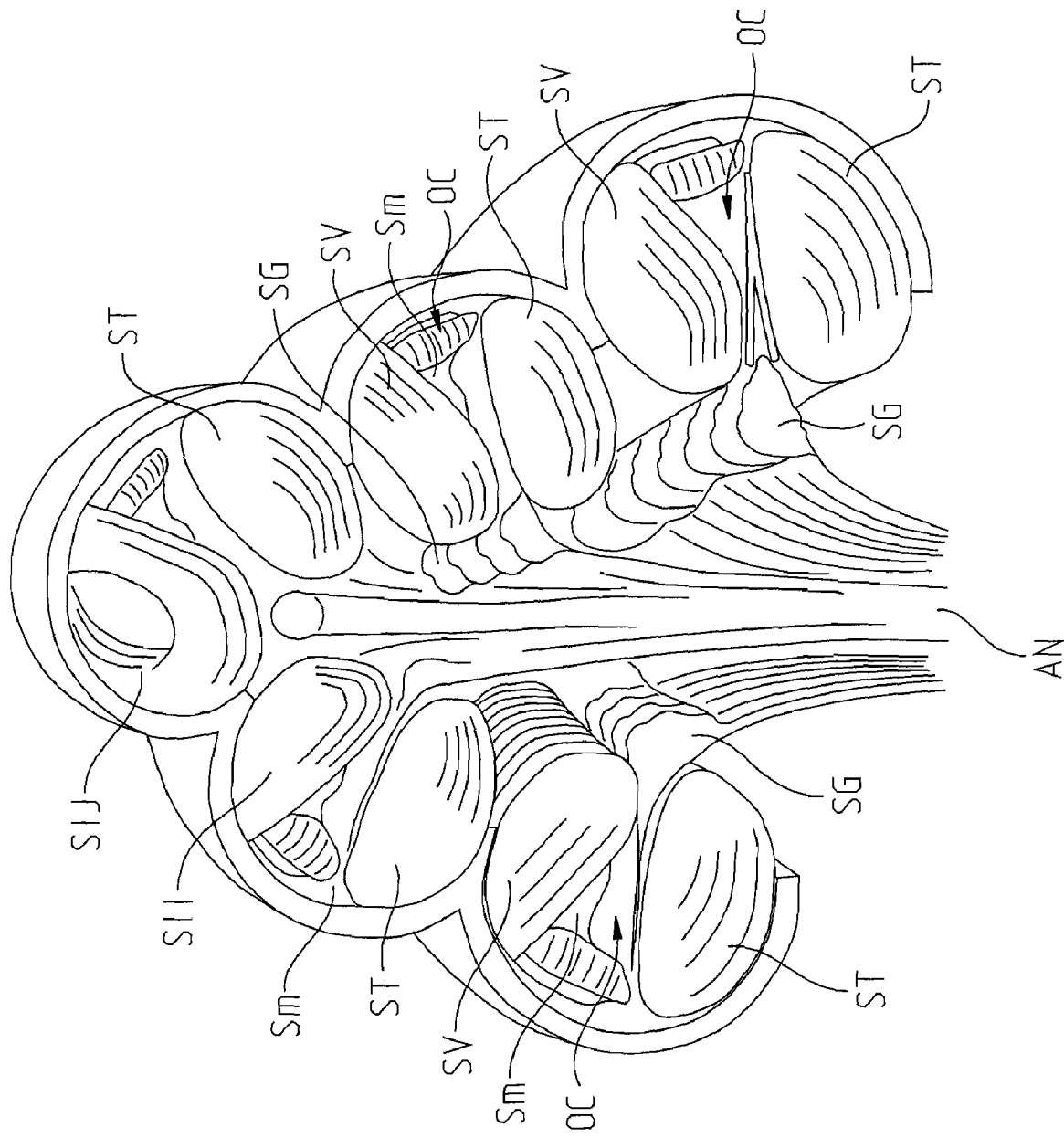
FIG. 1 is a diagrammatic sectional view through the cochlea in a plane parallel to and not far from the axis of the modiolus.
Figure 1A:
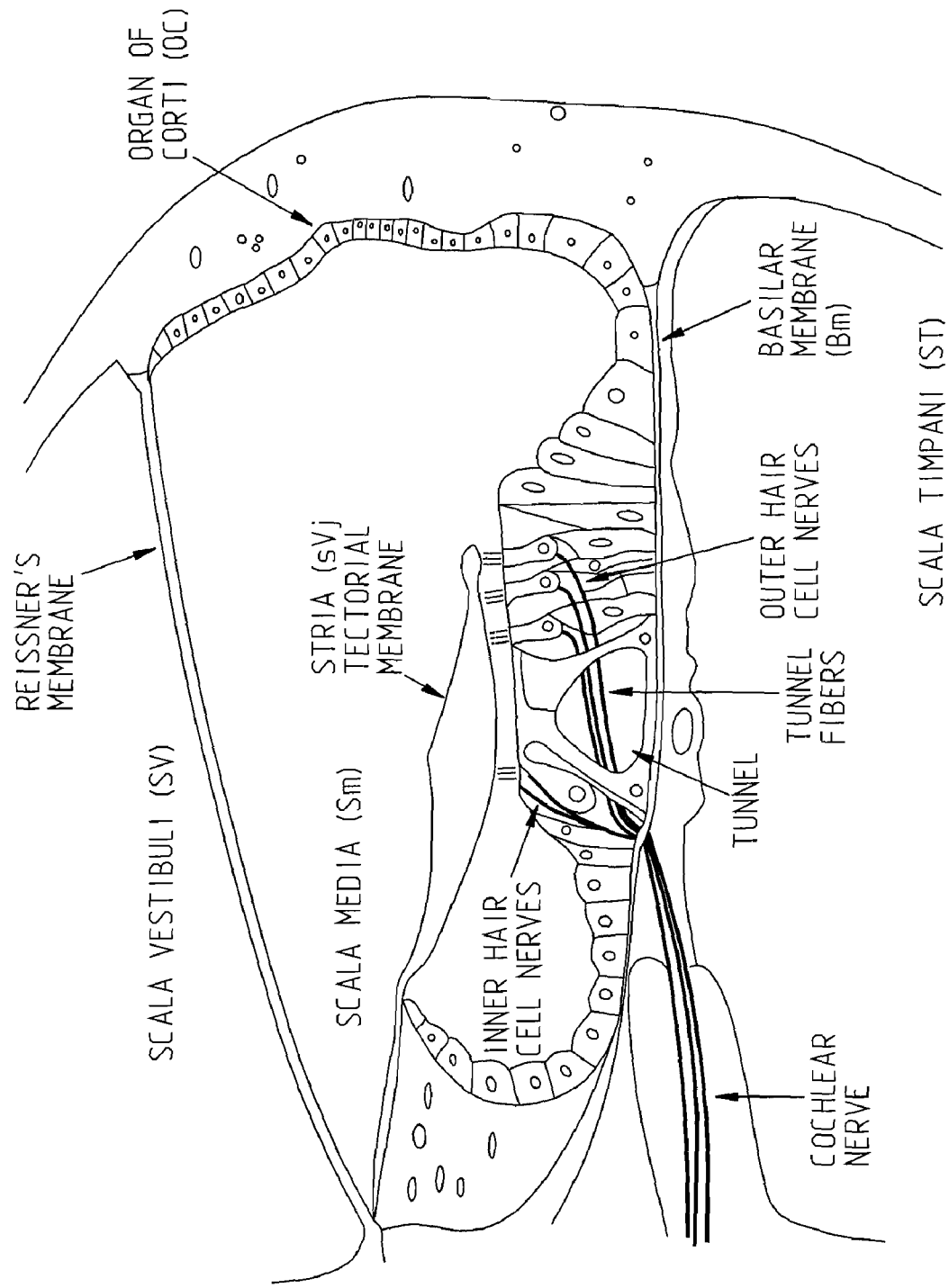
FIG. 1A is a sectional view of the cochlea's Organ of Corti.
Figure 2:
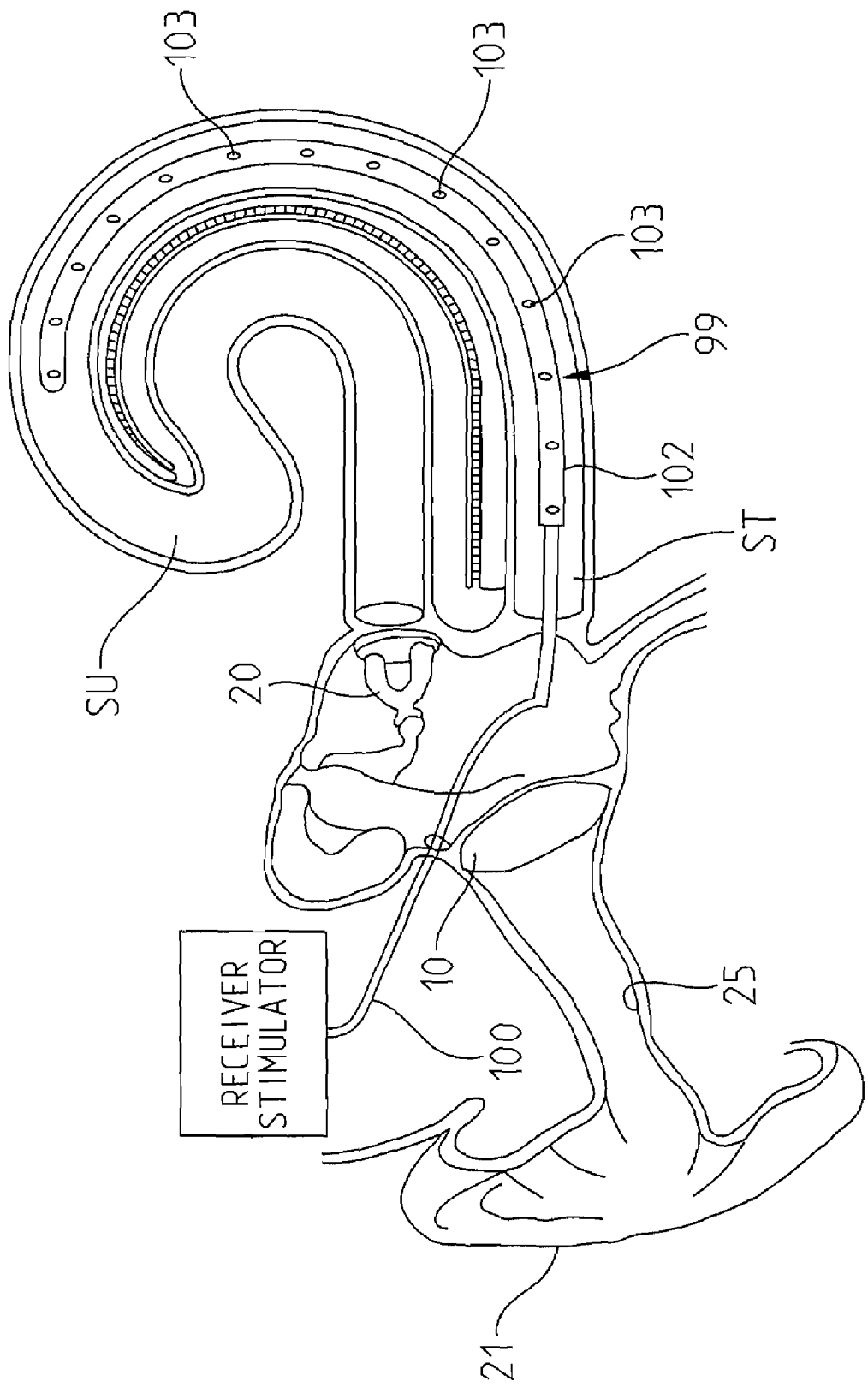
FIG. 2 is a diagrammatic side view of a prior art implant inserted within the scala tympani of an ear.
Figure 3:
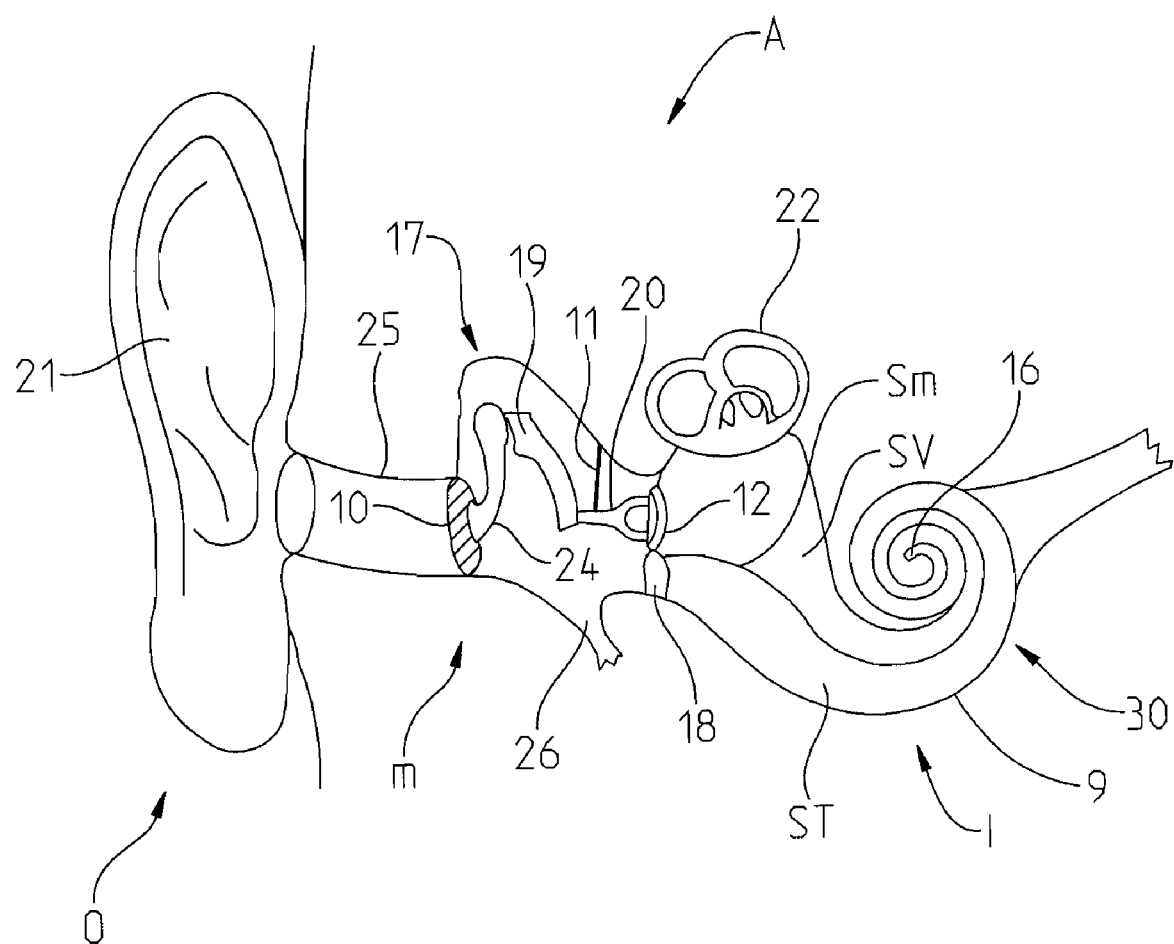
FIG. 3 is a macro-view of the anatomy of an ear, drawn somewhat diagrammatically.
Figure 4:
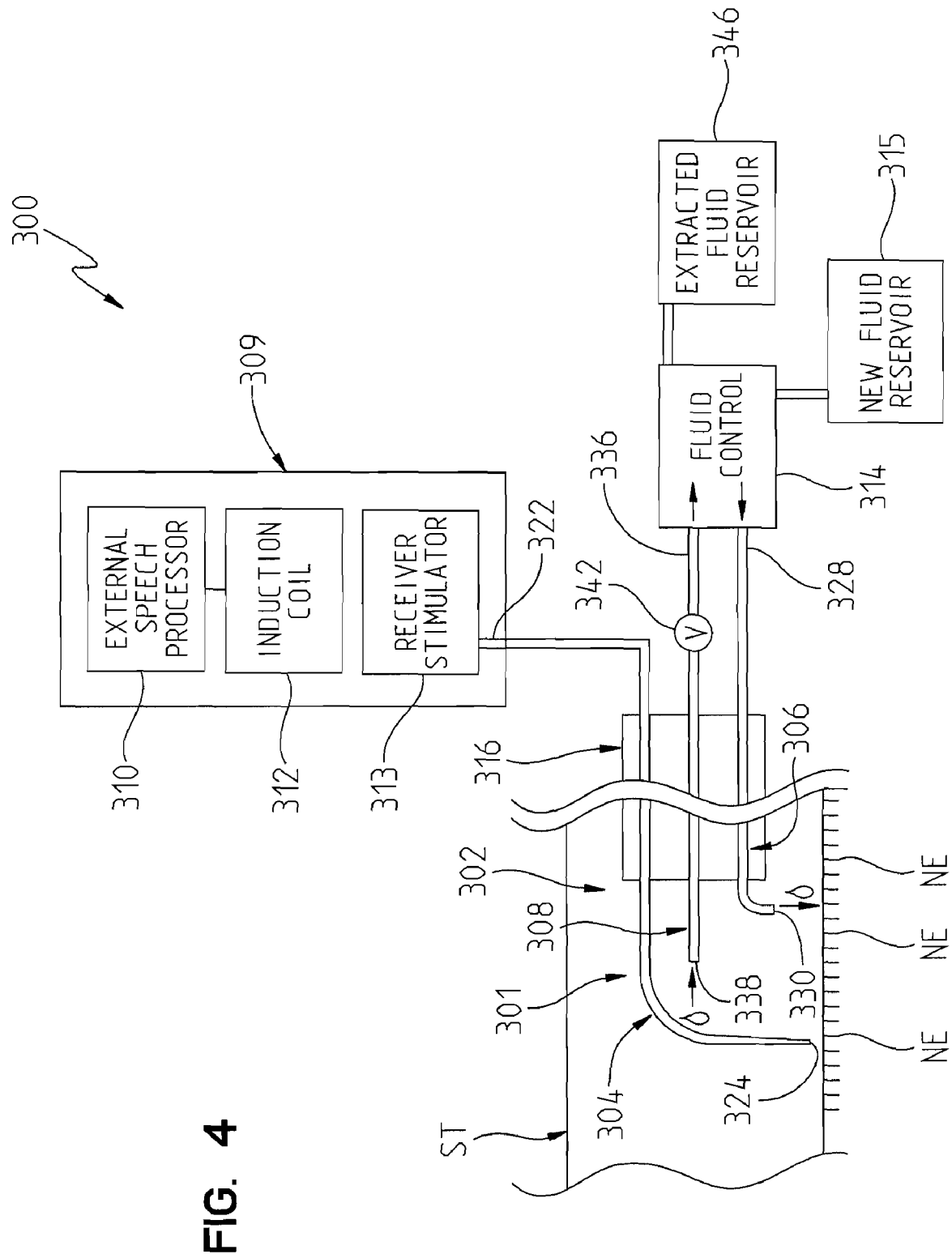
FIG. 4 is a schematic view of the intra-cochlear implant system of the present invention.

A schematic view of the intra-cochlear implant system 300 of the present invention is shown in FIG. 4, it being understood that the view in FIG. 4 is drawn highly schematically to acquaint the user with the primary components of the device.

The implant system 300 includes an intra-cochlear implant 302 that is designed for implantation preferably within the scala tympani ST of the cochlea, although it may also be placed with the scala vestibuli SV or scala media (also known as the cochlear duct) SM of the cochlea. In FIG. 4, the implant 302 is placed within the scala tympani ST. The implant 302 comprises a body portion 301 comprised of a bundle of electrodes that includes a large number of individual electrodes, as represented by electrode 304 for conducting a signal to an internal area of the scala tympani ST that is preferably adjacent to the hair-like nerve endings NE of the Cochlea, Organ of Corti OC, and spiral ganglion cells of the cochlea. The body 301 has a primary axis defined by the axis of the bundle of electrodes 304.

The implant 302 also includes inflow tubes 306 that are provided for delivering fluid through a fluid control device 314 for deposition within the interior of the scala tympani ST. The fluid control mechanism 314 may include a fluid reservoir 315 for supplying fluid to the fluid reservoir, and ultimately, to the inflow tube 306 and the interior of the scala tympani ST.

The electrode 304 is preferably coupled to an external speech processor 310 that is provided for serving as a transducer for converting sounds that the user may wish to hear into an electrical signal that can be induced into the electrodes 304 by an induction coil 312 and can be transmitted by the electrode 304 to the interior of the scala tympani ST, and preferably to a position within the scala tympani ST adjacent to or touching a nerve ending receptor NE.

A sheath 316 can be provided for partially encasing the electrode 304, inflow tube 306 and outflow tube 308 to maintain the tubes 206, 308 and electrodes 304 within a bundle. Depending on the design of the implant 300, the sheath 316 may extend along the full length of the implant 300, or alternately, may extend only partially along the length of the implant system 300.

The electrode 304 includes a proximal end 322 that is coupled to the induction coil 312 and receiver stimulator 313, or otherwise can be coupled to some other appropriate component of the signal generator 309 that can include the external speech processor 310 and induction coil 312 and receiver stimulator 313. A distal end 324 of the electrode is disposed within the interior of the scala tympani ST. For reasons that will be discussed in more detail below, the distal end 324 of the electrode 304 is preferably disposed adjacent, or reasonably close proximity to or touching the nerve ending receptors NE, so that the signal that is transmitted from the distal end 324 of the electrode 304 is delivered by the distal end 324 in a close, spatial relationship to the nerve ending receptors NE of the cochlea, Organ of Corti OC, and/or spiral ganglion cells.

The inflow tube 306 also includes a proximal end 328 that is fluidly coupled to the fluid control device 314 and a distal end 330 that is disposed within the interior of the scala tympani ST. The inflow tubes 306 conduct desirable fluid from outside the cochlea to the interior of the cochlea. These fluids can comprise a variety of substances, as will be discussed in more detail below such as neurotrophins, that when delivered to the interior of the cochlea ST, will help to stimulate nerve growth to help repair damaged nerve ending receptors NE to thereby promote better hearing.

The outflow tube 308 also includes a proximal end 336 that may be disposed at the fluid control device 314, or alternately can be disposed within a body cavity. The distal end 338 of the outflow tube 308 is disposed within the scala tympani ST. The outflow tube 338 conducts fluid away from the interior of the cochlea. For example, the outflow tube may be utilized to conduct fluid out of the interior of the cochlea, to ensure that the fluid level within the cochlea is balanced in view of the fluid deposited in the interior of the scala tympani by the inflow tube 306.

Preferably, the electrode 304, inflow tube 306 and outflow tube 308 are comprised of much thinner members than the wire and tubular members used currently. Most preferably, the electrode 304, inflow tube 306 and outflow tube 308 are comprised of carbon nanotubes, although a possibility exists that the use of one or more joined nanotubes for the inflow tube 306 and outflow tube 308 may not be feasible for use with certain fluids, as the size of the molecules of the fluid may be too large to channel through a nanotube, in which case conventional materials may be used to construct the tubules.

Carbon nanotubes (CNTS) are alletropes of carbon. A carbon nanotube is usually a one atom thick sheet of graphite, that is called graphene, and is rolled up into a seamless cylinder with a diameter on the order of a nanometer. This results essentially in a one-dimentional nanostructure with a length-to-diameter ratio that exceeds 10,000. Such cylindrical molecules have novel properties that make them potentially useful in a wide variety of applications. They exhibit extraordinary strength, unique electrical properties, unique optical properties and are efficient conductors of heat.

There are two main types of nanotubes: single-walled nanotubes (SWNTs) and multi-walled nanotubes (MWNTs). Most single-walled nanotubes have a diameter close to about one nanometer, with a tube length that can be many thousands of times longer. To date, single-walled nanotubes with lengths up to the order of centimeters have been produced. Single-walled nanotubes exhibit important electrical properties that are not shared by multi-walled carbon nanotubes variants. Single-walled nanotubes can be excellent conductors.

Multi-walled nanotubes consist of multiple layers of graphene or other materials rolled on themselves to form a tube-shape. There are two models that can be used to describe the structure of multi-walled nanotubes. In the Russian doll model, sheets of graphene are arranged in concentric cylinders. In the parchment model, a single sheet of graphene is rolled even around itself resembling a square of parchment or a rolled-up newspaper.

The electrical properties of a nanotube can vary, depending upon the structure and material of the nanotube. The nanotube can be designed to be metallic, or otherwise can be designed to operate as a semi-conductor. Nanotubes also exhibit good thermal and optical characteristics.

The benefit of the use of carbon nanotube, for the electrodes 304 in the present invention, is that the use of nanotubes permits a significantly larger number of conductors to be contained within the size constraints imposed on the cochlear implant by the rather small diameter size of the cochlea.

As discussed above, molecular size and fluid flow considerations may prohibit the use of nanotubes in conjunction with the inflow tube 306 and outflow tubes 308 of the cochlear implant 302 of the present invention, in which case they may be constructed by conventional materials and methods and not nanotechnology.

Figure 4A:
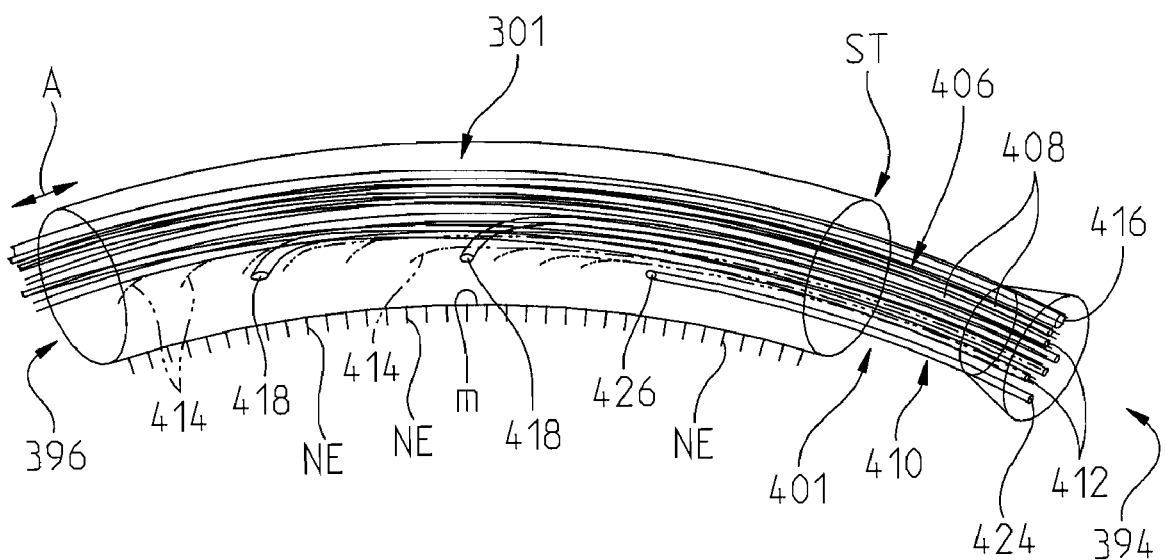
FIG. 4A is a diagrammatic view of a first embodiment of the intra-cochlear implant of the present invention.

A first embodiment of the present invention is shown at FIG. 4A as comprising an intra-cochlear implant 401 that is designed for being received within the scala tympani ST, so that signals given off by the electrodes 406 in the device can impact and send an electrical signal to the hair-like nerve ending receptacles NE of the cochlea, Organ of Corti and spiral ganglion. The implant 401 includes a body portion 301 having a proximal end 394, a distal end 396 and a primary axis A. The implant 301 includes a plurality of preferably nanotube type electrodes 406, one or more inflow tubes 408 for conducting fluid from outside the cochlea into the interior of the cochlea; and an outflow tube 410 for conducting fluid from within the cochlea scala tympani ST, to some place exterior of the cochlea. The electrodes 406 each include a proximal end 412 that can ultimately be coupled to a signal generator 309, such as is shown in FIG. 4. The electrodes 406 also include distal ends 414 that are preferably placed in close proximity to or touching the nerve ending receptors NE.

The inflow tube 408 includes a proximal end 416 and a distal end 418 that may be nanotube-type size, or alternately, may be a very small tube, that is as small as possible, while still having a sufficiently sized internal diameter so as to enable fluid of a desired type to be passed therethrough. The outflow tube 410 includes a proximal end 424 and a distal end 426. In certain cases, when certain fluids are being introduced into the scala tympani, such as neurotrophins, it is preferable to place the distal ends 418 of the inflow tube 408 in a position that is located close to the nerve ending receptors NE, so that the fluid materials dispensed by the inflow tube 408 will be deposited close to the place within the cochlea where the chemicals can have the most beneficial effect.

A sheath 430 can be provided for maintaining the large number of nanotube-sized electrodes 406 and ultra-miniaturized inflow tube and outflow tubes 408, 410 within a bundle. As discussed in connection with the discussion relating to the schematic view of FIG. 4, the sheath may extend over a portion of the implant 401, or alternately, over its entire length.

A primary difference between the electrode shown in FIG. 4 and the prior art resides in the existence of electrode 401 stimulating distal end 414 "brush-ends" and hollow conduit "tubules" 408, 410. These structures 406, 408, 410 have their proximal base ends 412, 416, 424, respectively positioned within the intra-cochlear electrode bundle and their distal ends 414, 418, 426 extending radially outwardly from the implant mass, and into the cochlear fluids and even touching the modiolus M. Preferably, the distal ends 414, 416, 426 of the brush-ends and tubules are as close to the cochlea nerve elements such as the ganglion cells and dendrites as possible. However, some of the distal ends may terminate within the fluids of the cochlea, touch the osseous spiral lamina, touch the modiolus structures, penetrate the endosteum or bone on the modiolus side, contact the spiral ganglion cells NE or even contact the cochlear nerve. In the two forms shown, the implant 401 of the embodiment of FIG. 4A floats within the cochlea, and the implant 432 of the embodiment of FIG. 4B touch the modiolus M due to a contour enhancing "spine" 434. Spine 434 can be bent or can be formed to impart a curvi-linear primary axis to the implant 432 so that the implant will be contoured to hug the modiolus.

The implant 401, 432, the electrode 406, the distal brush-ends 414, and tubules 408, 410 are micro- and nano-sized so that they do not take up much space. The distal brush-ends 414 can be placed close together so that they give very precise stimulation points to the cochlea nerve elements, spiral ganglion NE and cochlear nerve. The lengths of the individual electrodes 406 and tubules 408, 410 may be varied and different from one another and also from one electrode design to another particular design, depending on the specific needs and the limitations, some possibilities of which are discussed below. Also, the distal brush-ends 414 and tubule distal ends 418, 426 may be curved. Long curvy brush-ends 414 and tubule distal ends 424, 426 extend and become disposed radially outwardly from the center of the implant 401, 432 and hence, are capable of becoming positioned closer to the nerve ending receptors NE. By contrast, reducing the length of the curved distal portions of the electrodes 406 and tubules 408, 410 maintains the ends relatively radially inwardly and close to the axis of the implant 401, 432, and as such, are less likely to cause trauma to the tissue structure of the cochlea. The electrodes may be in clusters or alone. See, for example, the clusters of carbon nanotubule electrodes shown in Alan M. Cassell, *Ultrasensitive Carbon Nanoelectrode Biosensor Technology*, Center for Nanotechnology, UC-Santa Cruz, 22 Apr. 2004.

The electrodes 406 are electrically conductive members whose purpose is to transmit an electrical stimulus from a signal generator to the nerve elements NE, so that the electrical stimulus from the implant 401, 432 can electrically stimulate a nearby dendrite, ganglion or circumscribed neural tissue. Although the entire length of the electrode 406 is preferably comprised of a nanoelectrode-sized conductor, the electrodes 406 may comprise micro-sized wire conductors having a nano-sized distal end portion. The inflow and outflow tubules 408, 410 may also be electrically conductive.

An example of a nano-electrode that can be employed in connection with the present invention is a carbon nanotube that serves as an electrode. Carbon nanotubes have several advantages when used in the present invention, as carbon nanotubes have a high mechanical strength, and are approximately three times stronger than steel. Additionally, carbon nanotube electrodes are generally bio-compatible, as are other carbon electrodes currently used in situations were biocompatibility is necessary. Additionally, carbon nanotubes have a high electrical conductivity that is similar to graphite, and can be made to have very small diameters, such as between about 10 and 100 nano-meters. Additionally, an open carbon nanotubule end can be covalently fuctionalized.

In one embodiment the electrodes and nanotubules and then contents are designed to carry signals originating from the receiver-stimulator and the signal conducted is light. The electrodes and nanotubules are members that are light carrying channels. They are similar in function to fiber-optics, except that they are nanosized. The light is carried to the nerve endings cells and induces a photo-electric response in them. Cells are well known to fluoresce and otherwise grow under photo-stimulation. Thus, upon a sound wave being captured by the external device, the implant signals the inner ear nerve endings and cells with light, followed by the signaled nerve endings and cells transforming the light signals to electrical signals to the acoustic nerve for hearing sensation. The light signals are also used to stimulate growth of structures within the cochlea.

It is believed that fabrication techniques exist for fabricating carbon nanotubules of the type that will function in connection with the present invention, as the growth of the tubules can be controlled with PECVD techniques. For example, vertically oriented multi-wall, carbon nanofiber arrays have been grown to date by DC PECVD. See Allen M. Cassell "Ultra Sensitive Carbon Nano Electrode Biosensor Technology", Center for Nanotechnology, University of California at Santa Cruz, Moffitt Field, Calif. 22 Apr. 2004.

The tubules 408, 410 are tiny, hollow conduit tubes that are conceptually similar to fluid catheters and hypodermic needles. The inflow tubules 408 include hollow passageways through which many chemicals, medications, molecules, neurotrophins, protein-containing fluid nucleotides, and cells can be introduced into the interior of the cochlea. The outflow tubules 410 also include hollow passages through which excess fluid can be removed from the interior of the cochlea. The tubules are sized according to the size of the fluid contents to be administered. Thus, tubules sending cells would be large enough to carry them without obstructing the tubule.

The importance of having the distal ends 414, 418, 426 of the electrodes 406 and tubules 408, 410 close to the spiral ganglion is that their actions are enhanced. Ideally, the distal ends 414, 418, 426 are placed in a non-disruptive way close to pertinent anatomy like the Osseous Spiral Lamina, Modiolus, Organ of Corti, and cochlear duct so that the remaining anatomy is undisturbed. The length of the curvy distal portion of the tubules 408, 410 and electrodes 406 are designed to reflect the distance from the axis of implant to the endosteum, dendrites, and to the inner ear structures and be protective by not destroying sensitive anatomy in a "bulldozer" fashion when the implant 401, 432 is inserted into the cochlea.

The materials used to make the brush-ends 414 (FIGS. 4A, B, and 5) and tubules 410, 418, 426 are nanotubes alone or may include nanotubes combined with conventional materials and metals that are micro-cast, spun, tooled, printed and stamped. New materials such as metals, alloys, and carbon "nanotubes" and nano-based "quantum wire" and "quantum cables" are used. Some carbon-based nanotechnology is capable of conducting electricity even better than ordinary metals. Other materials conduct light similar to currently known fiberoptics. Examples of some wires and cables are related to those nanotechnologies have been manufactured by Richard Smalley at Rice University, as well as, those previously described by Allen M. Cassell, April, 2004, supra. The purpose of using these nanomaterials is that they allow for a smaller diameter electrode 401 entering the cochlea, which therefore provides the potential for a larger number of stimulating electrode distal end studs 414 and a perfusion system provided by the inflow 408 and outflow 410 tubes.

The implant 401, 432 has a relatively large transition area where the sheath 430 expands to connect intracochlear electrode parts to extracochlea parts. The sheath 430 is the area inside of which the supply of wires and tubes for the electrodes 404 and tubules 408, 410 are found. The expanded diameter portion of sheath 430 is located outside the cochlea where the size constraints of the cochlea no longer apply. There is a "transition area" where the nano or micro-sized parts link to the macro-sized parts.

Another feature is that the electrodes 406 and tubules 408, 410 are arranged close to each other like the bristles of a fine caliber paint brush with comb-like projections next to each other. Thus, when the implant 401, 432 is inserted into the cochlea using the intra-cochlear surgery technique, one can have a larger number of electrodes 406 and tubules 408, 410 that are contained with a diameter small enough so that the bundle of electrodes 406 and tubules 408, 410 can be squeezed easily inside the cochlea. The micro- and nano-diameter or width of these electrodes 406 and tubules 408, 410 permits a sufficient number of electrodes 406 and tubules 408, 410 to be fitted into a bundle to permit the distal brush-like ends of the electrodes 406 and the distal ends of the tubules 408, 410 to be positioned along a significant portion of the length of the scala tympani, scala vestibuli, and scala media (cochlea duct).

The closer the distal ends 414 of the electrodes 406 are to the ganglion cells and other nerve ending receptors NE, the more specific of a target for the electrode stimulation pulse of electrical energy. This is the "distance from target" problem. In presently available (prior art) implants "distance from target" is overcome by a single method of "modiolar-hugging". Modiolar-hugging means that the intra-cochlear portion of the implant is configured to coil tightly around the modiolus M. In other words, it hugs the innermost coil of the snail shell-like cochlea. Prior art modiolar-hugging implants produce this "modiolar hugging" by having a preformed silicone coil shape that reconfigures its coiled shape when a straight stiffening wire is withdrawn. Also, they have only about a dozen mono- or bipolar modiolar-hugging electrodes, which limit the number of nerve end receptor sites that can be stimulated. Therefore, this design seeks to overcome the "distance from target" issue in several ways.

A first way that this "distance from target" problem is reduced by the present design is by configuring the electrodes 406 and tubules 408, 410 so that their distal ends 414, 418, 426 are positioned close to the modiolus M (FIG. 4). A signal transmitted by a more closely positioned distal end 414 of an electrode is more likely to hit its target receptor because it is closer. The distance from target problem is reduced through the distal ends 414, 418, 426 (FIG. 4) of the electrode 406 and tubules 408, 410 being brought closer to the dendrites and ganglion cells by configuring the distal ends 414, 418, 426 of the electrodes 406 and tubules 408, 410 to extend radially outwardly from the axis of the implant 401, 432 toward the walls, and in particular, the modiolus of the cochlea. Rather than a few ball-like stimulating studs placed flush to the implant, as is used in the prior art, the Applicant's invention employs numerous longer brush-like distal portion 414 of the electrodes 406 to stimulate the nerve elements. The non-modiolar hugging "regular" implant 401 embodiment shown in FIG. 4A floats within the fluids of the scala tympani ST, scala vestibuli SV, cochlear duct SM or any combination thereof, and is positioned farther away from the modiolus, dendrites and ganglion cells. By increasing the length and radially outward extent of the distal ends 414, 418, 426 of the electrodes 404 and tubules, the distal ends 414, 418, 426 will lay closer to the receptors at the stimulation target points. A "regular" type implant may also be able to benefit through the use of radially extending electrode 406 portions of its electrodes and tubules.

Figure 4B:
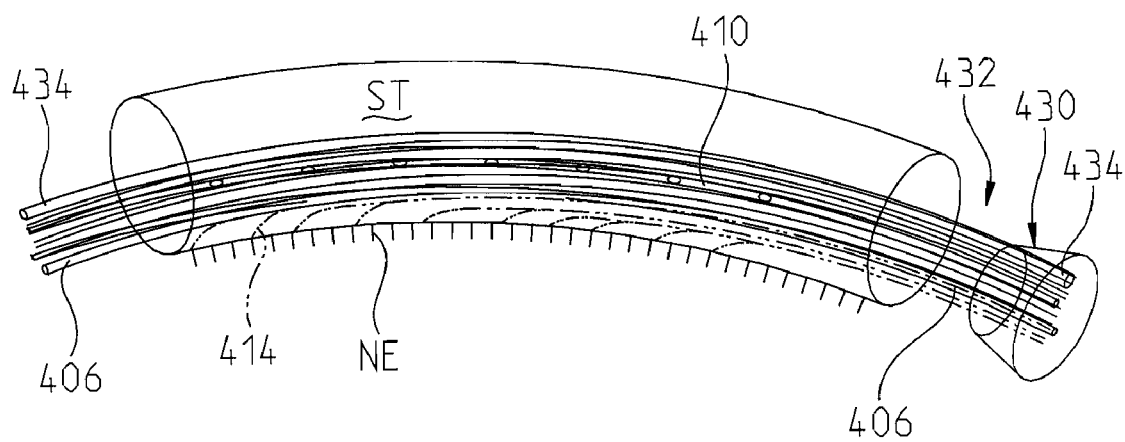
FIG. 4B is a diagrammatic view of a second embodiment of the intra-cochlear implant of the present invention.
Figure 5:
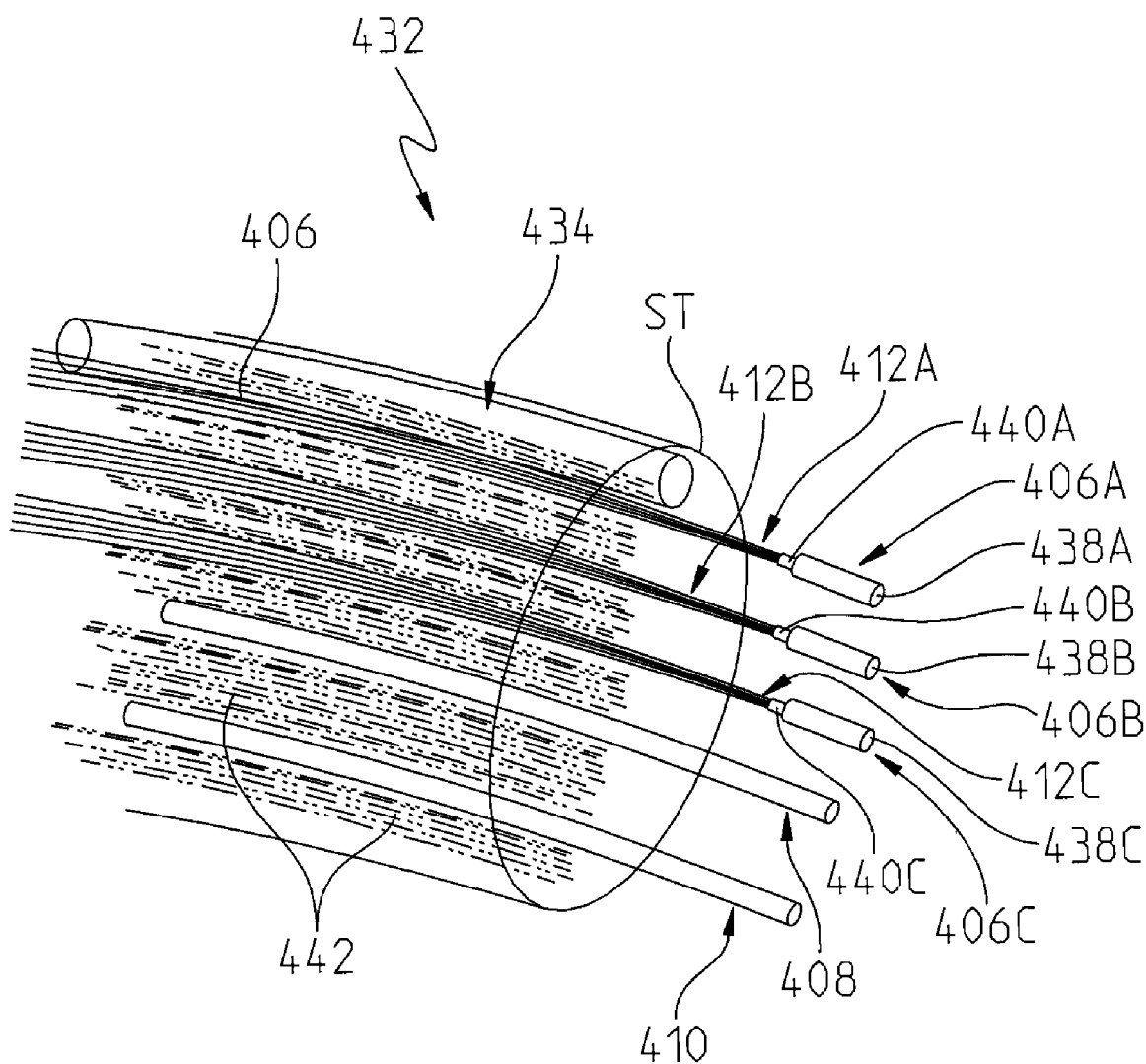
FIG. 5 is a schematic view of a portion of a cochlea having an implant of the present invention inserted therein.

A second way is shown in an enlarged view of the electrode 432 from FIG. 4B as the magnified view of 432 in FIG. 5. Electrode 432 includes a spine 434 that is comprised of nanofiber materials, wires, and cable. This spine 434 enables the implant to be bent or formed into a curving shape, so that, when inserted into the scala tympani ST, the implant will tend to hug the modiolis, to thereby place the distal brush-ends (not shown) of the electrodes 406 closer to the nerve ending receptors (not shown). The "hugging" may also only take place in certain areas associated with electrodes and tubules, so that the final shape may be like a coil made of a sinusoidal line.

In another embodiment, the intracochlear electrode is brought into a particular shape within the cochlea by use of a shape-memory metal within the spine 416 (FIG. 4A), 434 (FIGS. 4B, 5). The intermetallic substance is an alloy of mainly titanium and nickel and is commercially available and known as "Nitinol". Nitinol is a nickel-tilanium alloy, which is a shape-memory alloy that remembers its original shape or geometry. After it is deformed, Nitinol regains its original shape during heating. The implant employs use of the Nitinol in its "spine" area (FIGS. 4A,B; 8-A; 8-C). The spine area is specifically attached to or imbedded within the implant to shape the final position of the implant within the cochlea. The desired shape may result in an implant position that is towards the lateral-outer side of internal cochlea away from the modiolus, or towards the inner side, close to the modiolus, or in an intermediate position. The final shape can allow for the placement of the electrode into various scala and piercing several layers of intra-cochlear tissue, all within one implant final position. Also, it may be used to accommodate several simultaneous implants within the cochlea. The Nitinol is activated by heat to restore itself to an original shape that had been deformed. The shape-memory is repeatable.

A third way that the "distance from target" problem is overcome is to place each individual stimulating electrode brush-end or tubule closer to its set of target-nerve endings. In the view shown in FIG. 4, nanofiber electrodes brush-ends 414 (FIGS. 4A, B) are shown. It will be appreciated that a much larger number of nano electrode brush-ends are used in practice than shown. In practice, it is envisioned that greater than fifty electrodes 414 will be employed, and preferably approximately 10,000 or more electrode brush-ends will be possible. By increasing the number of electrodes 414 by using nano-wires, cables and filaments, a huge increase in the number of stimulating sites arises with the present invention 401, 432 implants. Each of the electrode brush-ends 414 are individually closer to their respective target nerve endings and help overcome the distance from target problems. The stimulating electrodes must be eventually joined with the signal generator unit 309 (FIG. 4). This is much different from the prior art where a dozen or less electrodes are responsible for stimulating the entire cochlea's 30,000 hearing cells, and are relatively distant from their respective target nerve endings.

Each of the nanotubule electrodes 406A, 406B, and 406C (FIG. 5) have a proximal end 412A, 412B and 412C. At the proximal ends 412A, 412B and 412C, the nanotubule fiber bundles are joined to an electrical conductor, such as electrical conductors 438A, 438B and 438C respectively, by junctures 440A, 440B and 440C. The conductors 438A, 438B and 438C are then directed to the speech processing and induction coil devices described above and shown in FIG. 4. It will be appreciated that a much larger number of nano-electrodes are used in practice than are shown.

A fourth vehicle for reducing "distance from target" problems is achieved by both the "regular" 401 and "modiolar-hugging" 432 implants by having nerve and organelle growth stimulating agents associated with their design and function. The growth agents are intended to stimulate dendrites, nerve tissue, and hearing organelles into being, growing, cell division, multiplying, and reconstituting hearing anatomy. Further, these new anatomic structures grow toward the source of their stimulus. Therefore, the implant 401, 432, electrodes 406, stimulation points 414, and fluid tubules 410, 418, 426 can be in proximity to, enveloped in, touch, and connected into these anatomic structures and new anatomic parts.

Proximity between implant and nerve endings and direct connection between them are important because better and selective stimulation of hearing occurs. Also, less energy is needed to stimulate the nerve ending receptors NE. Practically, this translates into better hearing thresholds, better sound spectrum, better understanding and longer battery life.

Figure 6:
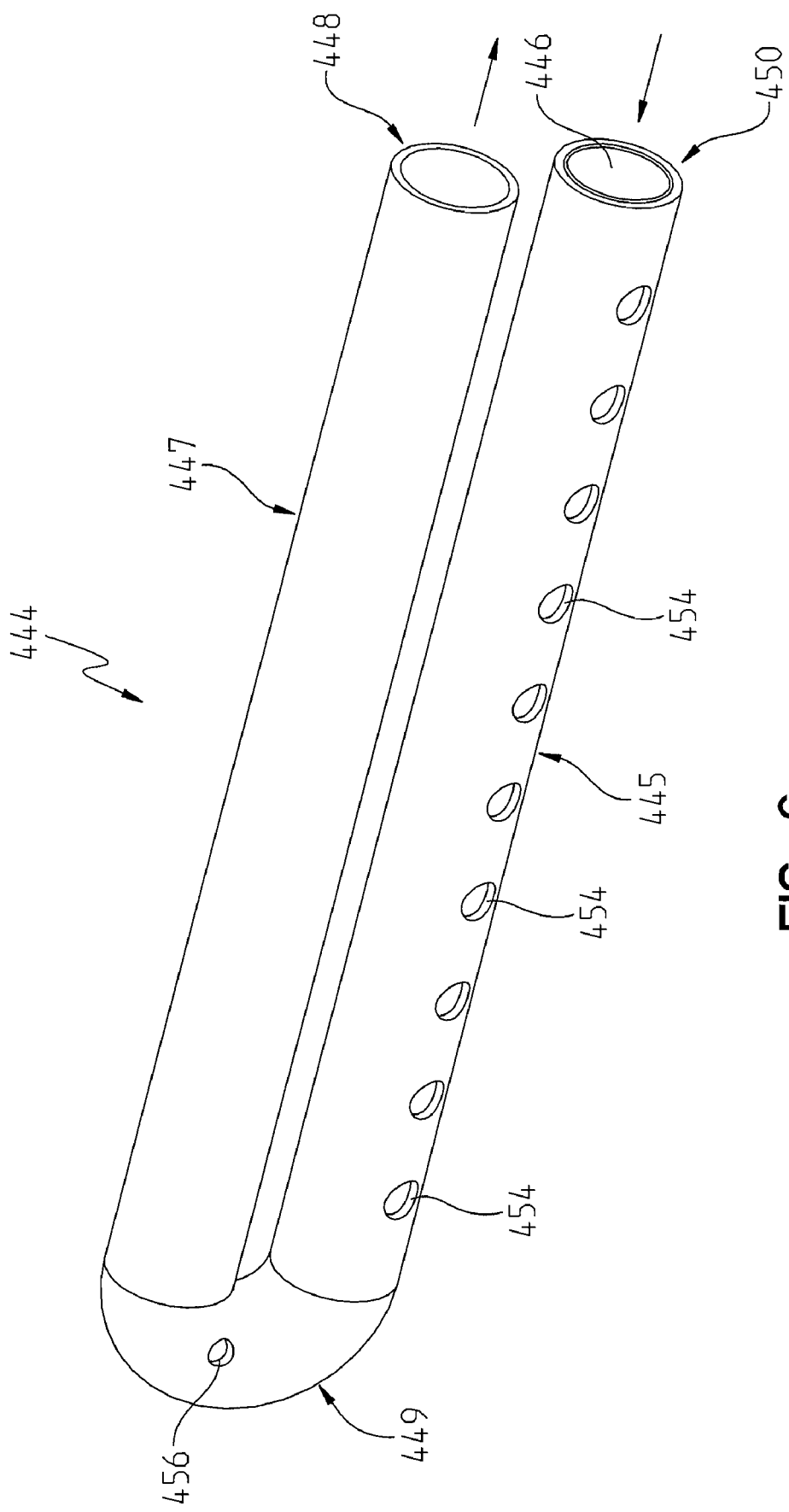
FIG. 6 is a greatly enlarged side view of a fluid-carrying tubule of the present invention that can be designed to be a part of the intra-cochlear implant of the present invention.

The electrode hollow tubule 408 (FIG. 4) can be used as a conduit for infusing fluid. In FIG. 6, a U-shaped hollow tubule 444 of the type that can be used in place of inflow tubules 408 and outflow tubules 410 of FIGS. 4A and 4B is shown. Tubule 444 is generally U-shaped, and includes an interior passageway 446 through which fluid can pass in to tubule 444. The tubule includes an inflow portion 445 that terminates at its upstream end at a first inflow end 450. The tubule 444 also includes an outflow portion 447 that terminates at its distal or downstream end in a second or outflow end 448. A bent portion 449 is generally U-shaped, and joins and fluidly couples the inflow portion 445 with the outflow portion 447.

The inflow portion includes a plurality of fluid dispensing apertures 454 that place the interior passageway 446 in fluid communication with the interior fluids of the interior fluids of the interior of the scala tympani ST or other scala. As fluid flows through the inflow portion 445, the fluid passes out of the apertures 454, and into the scala tympani ST. One or more fluid uptake apertures 456 is provided, either in the bend portion 449, or in the outflow portion 447. The fluid uptake apertures 446 place the fluids within the scala tympani in fluid communication with the interior passageway 446. The uptake apertures 456 are provided for receiving fluid that can flow into the uptake apertures 456, and then flow into the interior passageway 446, and be conducted out of the cochlea by the outflow portion 447. In this way, the amount of fluid being deposited within the scala tympani through the fluid dispensing aperture 454 can be equalized with the amount of fluid being removed from the scala tympani by the uptake apertures 456, so that the amount of fluid (and hence fluid pressure) within the scala tympani will generally remain constant.

The U-shaped tube 444 is preferably either a nano-catheter, or a micro-catheter. In the embodiment shown in FIG. 6, the perforations 454 along the length of the inflow portion 445 allow egress of infused fluid into the cochlea.

The tubule 444 serves as a catheter that is designed to deliver different types of chemicals and cells (e.g. neurotrophins, antioxidants, chemicals, medications, vasoactive compounds, growth factors, nucleotides, RNA, DNA, amino-acids, nutrients, cells, stem cells, "nanobots" or nano-robots). The purposes of the infused substances are to attract and give rise to nerve growth from the spiral ganglion and cochlear nerve towards the actual stimulating brush-like distal ends of the electrodes 406 (FIGS. 4A, B), improve the health of the remaining cells, alter growth of cells, and to create new cell and organ growth. Additionally, substances such as medications, antibiotics, antifungals, hormones, anti-seizure, growth hormone, libido enhancement and other substances that act on specific organs or the entire organism may be delivered.

As will be appreciated, the compounds discussed above are comprised of molecules of different sizes. One factor that will influence the size of the interior diameter of the tubule 444 that is used for the implant to deliver these compounds will be the size of the molecule of the compound being delivered. Smaller molecules (e.g. electrolytes; $Na^+$; $K^+$, $Ca^{++}$, $Mg^+$) will be small enough to pass through nano-sized tubules, whereas very large molecules (e.g. DNA, RNA) or cells will require "micro" sized tubules.

The infusion of the substances would optimally cause nerve cell growth such that one or more brush-like distal ends 414 (FIGS. 4A, B) would become wrapped in nerve tissue and very easily and efficiently transmit the impulse with minuscule amounts of electrical power directly to the nerve. The purpose of the various chemicals, neurotrophins, DNA, RNA and infused cells, and stem cells, is to provoke, nurture, feed, stimulate, and seed cellular growth of new internal cochlear anatomy. The new anatomy can serve as either a replacement of damaged anatomy or, can comprise wholly new structures in new areas not found in normal cochlear anatomy. It is noteworthy that placement of a catheter or infusion of substances and cells into certain areas will allow for creation of wholly new anatomy in areas not naturally found in nature. Examples would be a new and stimulateable set of dendrites in the scala vestibuli, scala tympani, scala media, modiolus, acoustic nerve, or a stimulateable Organ of Corti growing in the scala tympani. There may be more than one type of new anatomy within each of the scala, or anchored to the modiolus, basal membrane, stria vascularus or other areas.

In the embodiment shown in FIGS. 4A, B and 5, multiple numbers of micro- and nano-sized catheters 408, 410 are employed that end at various points along the electrode to nourish different areas along the scala tympani, and hence different areas of nerve ending receptors. At the sheath 430, they would join a catheter system originating in a reservoir (FIG. 4). An exit catheter(s) would allow for fluid to leave the cochlea in roughly the same amount that is infused in order to relieve fluid pressure build-up.

A cochlear implant is meant to be a life-long device. With presently available devices though, there has been upwards of about a 10 percent failure rate, resulting in the need to replace some installed implants. So far, in presently available implants, removal of intra-cochlear electrodes and placing new ones has generally not shown a decline in patient performance. With these new proposed hearing aid implants of the present invention, replacement is an unknown situation because in removing the implant electrode, structures and nerve tissue may become shredded if the infusion of chemicals into the cochlea has been successful in causing nerves to grow onto and attach to the electrodes 406, brush endings 414, and tubules 408, 410. However, the anticipation is that the implant of the present invention would also be a life long device. Also, a replacement device would give rise to the same benefits of cell and nerve growth as the original device, and so any damage could heal quickly.

The device itself gathers its electrical energy through a trans-cutaneous induction coil 312 (FIG. 4) between the internal receiver-stimulator and the external speech processor 310. The external processor 310, the method of trans-cutaneous transmission, and the internal receiver-stimulator device that are employed with the present invention can be generally similar to those used in present implants, and will likely evolve along the same lines as the analogous devices used with other implants. The device may be connected directly through the skin with a percutaneous plug and mount.

Different from presently known implants is that the hollow tubules, e.g. 408 that supply fluids to the cochlea will need a supply tube and materials source. The materials source can take several forms such as a subcutaneous reservoir, a subcutaneous pump, a mini-osmotic pump such as or similar to the Alzet 2001 pump manufactured by the DURECT Corporation of Cupertino, Calif. The Alzet osmotic pumps are described as being miniature, implantable pumps that are currently used in research in mice, rats and other laboratory animals. These infusion pumps continuously deliver drugs, hormones and other test agents that control range from one day to four weeks without the need for external connections or frequent handling. If an Alzet-type osmotic pump is used, the pump would need to be equipped with a reservoir for refilling, or a transcutaneous tube for direct access to the pump.

Figure 7A:
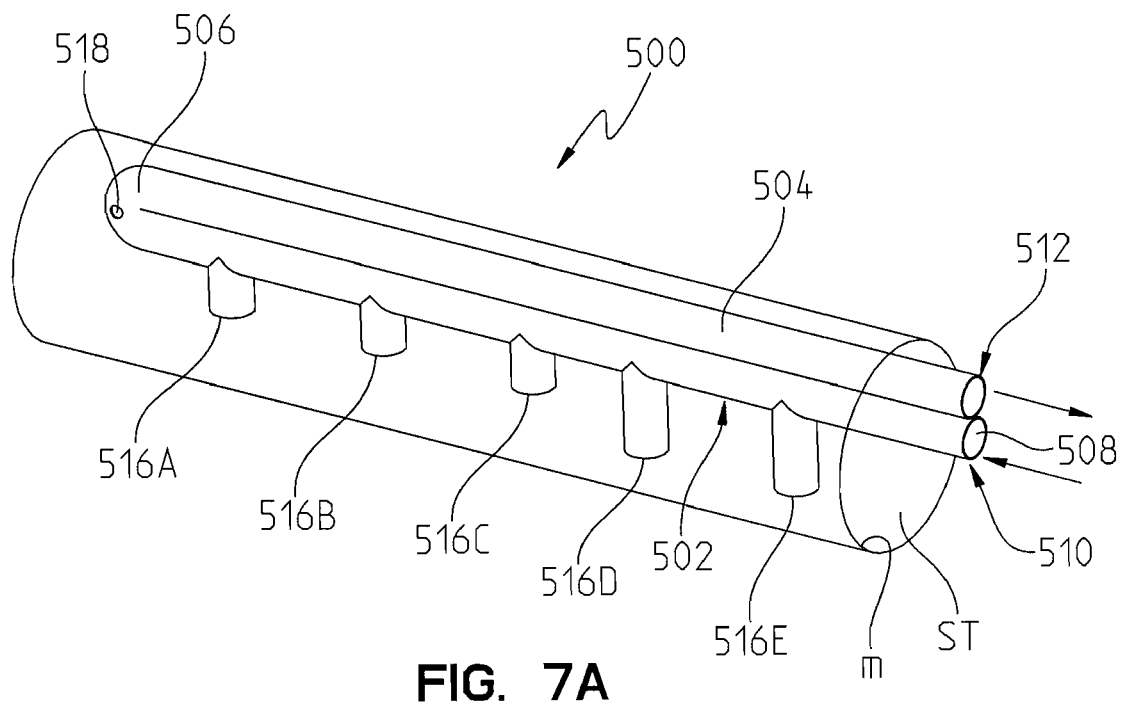
FIG. 7A is a diagrammatic view of a tubule member embodiment of the present invention for carrying fluid into and out of the cochlea, which tubules can be a part of the implant of the present invention.

Turning now to FIG. 7, other embodiments of tubule/catheter systems are shown. Turning first to FIG. 7A, a fluid conduit tubule 500 is schematically represented as being inserted within the scala tympani ST of a cochlea. The tubule conduit 500 is generally U-shaped similar to conduit 444 shown in FIG. 6, and includes an inflow portion 502, an outflow portion 504, and an elbow-shaped juncture portion 506, that couples together the inflow portion 502 and the outflow portion 504. Fluid flows within the hollow passageway interior 508 of the conduit in a direction indicated generally by the arrows. Appropriate fluids, such as those described above in connection with the device of FIG. 6 are directed into the inflow portion 508. The inflow portion includes a series of branches that comprise a series of shunts 516A, 516B, 516C, 516D and 516E that are disposed along the length of the inflow portion 502 for depositing appropriate fluids along the length of the scala tympani in which the fluid conduit tubule 500 extends. It will be noted that the shunts can be of different lengths, and, as schematically represented in FIG. 7A, shunts 516D and 516E are shown to be relatively longer than shunts 516A, 516B and 516C so that the distal ends of shunts 516D and 516E are disposed closer to the modiolus M, and hence the nerve ending receptor. An uptake aperture 518 is provided for placing the exterior and interior of the tube 500 in fluid communication, so that fluid may be taken into the outflow portion 504 and directed out of the interior of the cochlea.

Figure 7B:
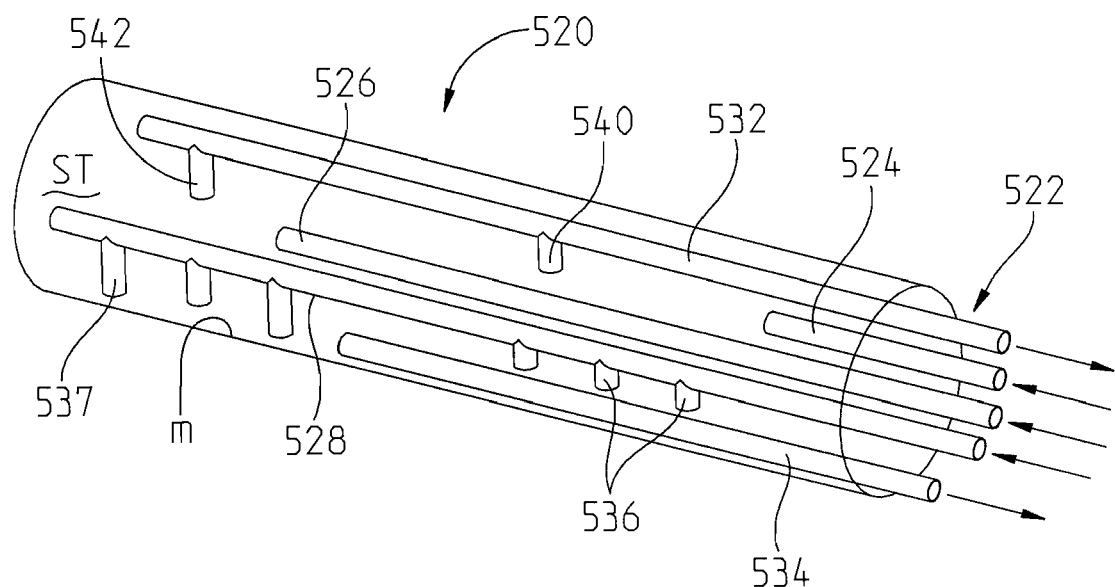
FIG. 7B is a diagrammatic view of a tubule member other embodiment for carrying fluid into and out of the cochlea, which tubules can be a part of the implant of the invention.

Turning now to FIG. 7B, another alternate embodiment fluid delivery and uptake system 520 is shown diagrammatically. The uptake and delivery system 520 of FIG. 7B includes a tubule conduit system 522 that includes a first inflow conduit 524, a second inflow conduit 526 and a third fluid inflow conduit 528, it being appreciated that many more inflow conduits may be employed in the actual device, depending upon space consideration. Additionally, there is first and second outflow conduit 532, 534.

FIG. 7B is important in that it illustrates that there may be mixed types of conduits being used. For example, a third inflow conduit 528 and first outflow conduit 532 are branch conduits that include a plurality of shunts. For example, the third inflow conduit 528 includes a plurality of shorter length shunts 536 and longer length shunts 537 for delivery fluids, such as neurotropins, etc., as described above into the interior of the cochlea. Similarly, first outflow conduit 532 also can include shorter 540 and longer 542 shunts for facilitating the uptake of fluid into the outflow conduit 532. Alternately, the first and second inflow conduits 524, 526, and the second outflow conduit 534 designed as "straight pipes" without the branches.

The purpose of FIG. 7B is to illustrate the various arrangements by which the conduits may be arranged to better deliver fluid to the cochlea, and more particularly, that portion of the cochlea close to the modiolus and the nerve and other tissue in need of regeneration. As alluded to above, different types of tubules may be used with different types of chemicals. For example, as neurotropins are preferably delivered close to the modiolus, so that they will be deposited close to the side of the nerve endings to promote nerve growth, it may be preferable to feed the neurotropins into the cochlea via tubes that have radially extending portions such as a shunt, to thereby deliver the neurotropins more efficiently to the area near where the neural endings reside.

Alternately, some chemicals may not need any specific placement and may be better delivered by the non-branched tubules. Additionally, tube type will also be determined by the size of the molecule being delivered as certain molecules or cells may be too big to deliver effectively through a nanotubule, but may require a micro-sized tubule or possibly larger.

Small catheter tubing would lead from the fluid source to the electrode sheath transition area 430 (FIG. 4B) and electrode tubules 408. The supply source and tubing, in one form, has a self-sealing, detachable valve attachment to the electrode and/or implant device.

One additional feature of the Applicants' particular electrode that may be necessitated by the introduction of fluid into the cochlea is an exit valve so that fluid can be removed from the cochlea in response to the fluid being placed into it. In practice, the fluid within the cochlea is non-compressible. There is some minimal "give" to the membranes and absorption of fluid. However, if one adds a volume of fluid to the cochlea and it has no where to go, one will not be able to add additional fluid. Therefore, one has to remove fluid as one injects fluid.

An outlet valve(s) can be provided to allow fluid to be removed. An outlet valve (such as represented by valve 342 in FIG. 4) can either be placed at a distant site through another small soft surgery area, or can be placed at one end of the described electrode pads, or it could be several valves along the electrode. The egress port (e.g. aperture 456 of FIG. 6) permits the egress of fluid. The exiting fluid would fill a separate reservoir (e.g. reservoir 345 of FIG. 4), shunt into the middle ear or mastoid tissues, shunt into surrounding soft tissue such as the temporalis muscle, shunt outwards through a trans-cutaneous tube, or shunt into the extra-dural, intra-dural or intra-cranial spaces. There may be use of a valve or valve system, an osmotic membrane, or combination thereof, and also a detachable self-sealing valve.

One benefit of using nanotechnology for the intra-cochlear device is that in addition to the nano-wire electrodes 406 (FIG. 4A), there are one or more fluid-containing conduits, e.g. 408, 410 that will also take up space. Since the smaller wires, cables, filaments and tubules of nanotechnology take up less space, the overall diameter of the implant can be made to have a sufficiently small diameter to still fit into the cochlea. Intra-cochlear implants are limited by the absolute, finite size of the interior of the cochlea, and in particular, diameter of any of the interior chambers of the cochlea. Therefore, it is important to miniaturize the components as much as possible. Nano-cables and wires help to achieve the miniaturization.

In another embodiment, the stimulating brush-ends or adjacent structures and tubules have a slow release compound or mechanism related to them. The compound can be coupled to the electrode 406 (FIGS. 4A, B) or fluid tubule 408, 410 either by placing a paste, coating, bonding; attaching a bulbous or shaped deposit; impregnating the material itself that is used to construct the brush-like distal ends 414, 418, 426 of the electrodes 406 and tubules 408, 410; or filling a hollow tubule. The compound preferably includes a pharmacologically active agent, that may be either chemical or cellular and may include such things as neurotrophins, antioxidants, medications, growth stimulants, nucleic acids, stem cells, etc., that is formulated into a slow release compound. By slowly dissolving or mechanically liberating these substances over a period of time, the neural growth or cell/organelle growth within the cochlea is accomplished.

One example among many of such a mechanism for slow release is a porous "Buckey Ball" of carbon atoms filled with the desired substance. Such a Buckey Ball is attached to the electrode 406 distal ends or the distal ends of the tubules 408, 410 or spine 434, would permit the desired substance to slowly leak out through the openings in the Buckey Ball. In one embodiment, the electrode may or may not have any supply reservoir and tube system connected with it. Rather, the chemicals and/or cells are delivered through the slow-release mechanism by itself. The slow-release mechanism could also be used in addition to the fluid infusion in the same electrode. Several different time lengths of release may be used.

The slow-release dissolving mechanism is also useful to keep the distal ends 414, 418, 426 of the electrodes 406 and tubes 408, 410 patent and free from obstruction during the insertion process. Cellular debris would be significantly less likely to plug the interiors of the hollow tubules or electrodes 406 since the slow release compound would shield against blockage.

The openings in the hollow fluid conduit tubules 408, 410 may take various forms. A single opening at the tubule distal end 418 (FIG. 4A) is one embodiment. An opening or several openings on the sides of the tubules such as openings 454, 456 of FIG. 6 is another embodiment. The openings may actually form a sieve-like mesh construction of the fluid conduits 408, 410. The openings may vary from fluid conduit tube to fluid conduit tube. Also, a continuous catheter-like tubule with openings 454, 456 along its length (FIG. 6) would allow for fluid flow into the cochlea with a return catheter (e.g. outflow portion 447), along the electrode or separate in another area of the cochlea.

The electrodes 406 and its parts are constructed of nano-technology, metals, noble-metals, alloys, plastics, fiberoptics, carbon-based compounds, bonding agents, welds, printed circuits, gels, gases, powders, slow and fast timed-release materials, nano-technology, nano-fibers, nanotubes, nanoconductors, quantum wires, quantum cables and nano-materials. The broad spectrum of nanomaterials and nano-products is used to improve the device. The nanotechnology may be used in combination with conventional technology as a type of "hybrid".

If one looks at the embodiments shown in FIGS. 4A and 4B, one will notice that there is a plurality of distal ends 414 of the brush-end-like distal ends 414 of the electrode, and there may be a plurality of fluid input and output tubules 408, 410. There are several potential mechanisms for delivering an electrical signal to the various distal brush-ends 414. As best shown in FIG. 5, the nanotechnology allows many quantum cables and fibers to pass down the implant 432. Some will carry signals, while others 442 may not. Those that do not carry electrical signals will act as insulation around those that do carry signals, to prevent the spread of current to adjacent electrodes. The small size allows for insulation fibers and layers between electrical conducting fibers and layers.

Figure 8A:
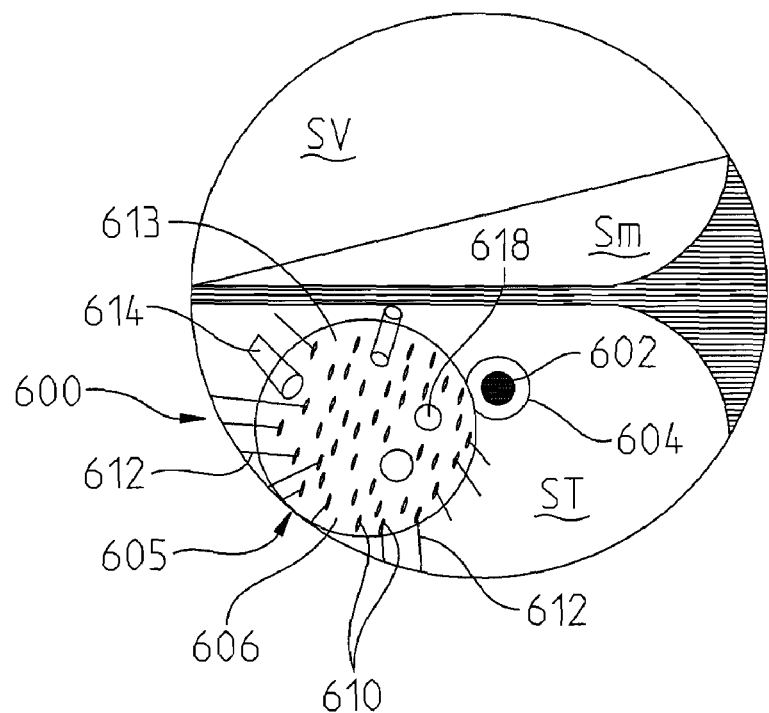
FIGS. 8A, 8B and 8C are cross-sectional diagrammatic views of various manners in implant of the present invention can be placed within the cochlea of a patient.
Figure 8B:
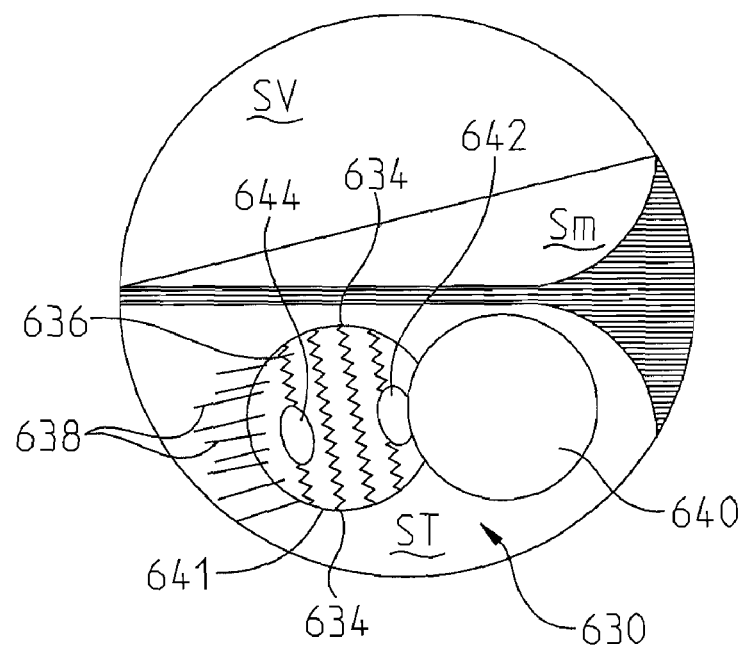
Figure 8C:
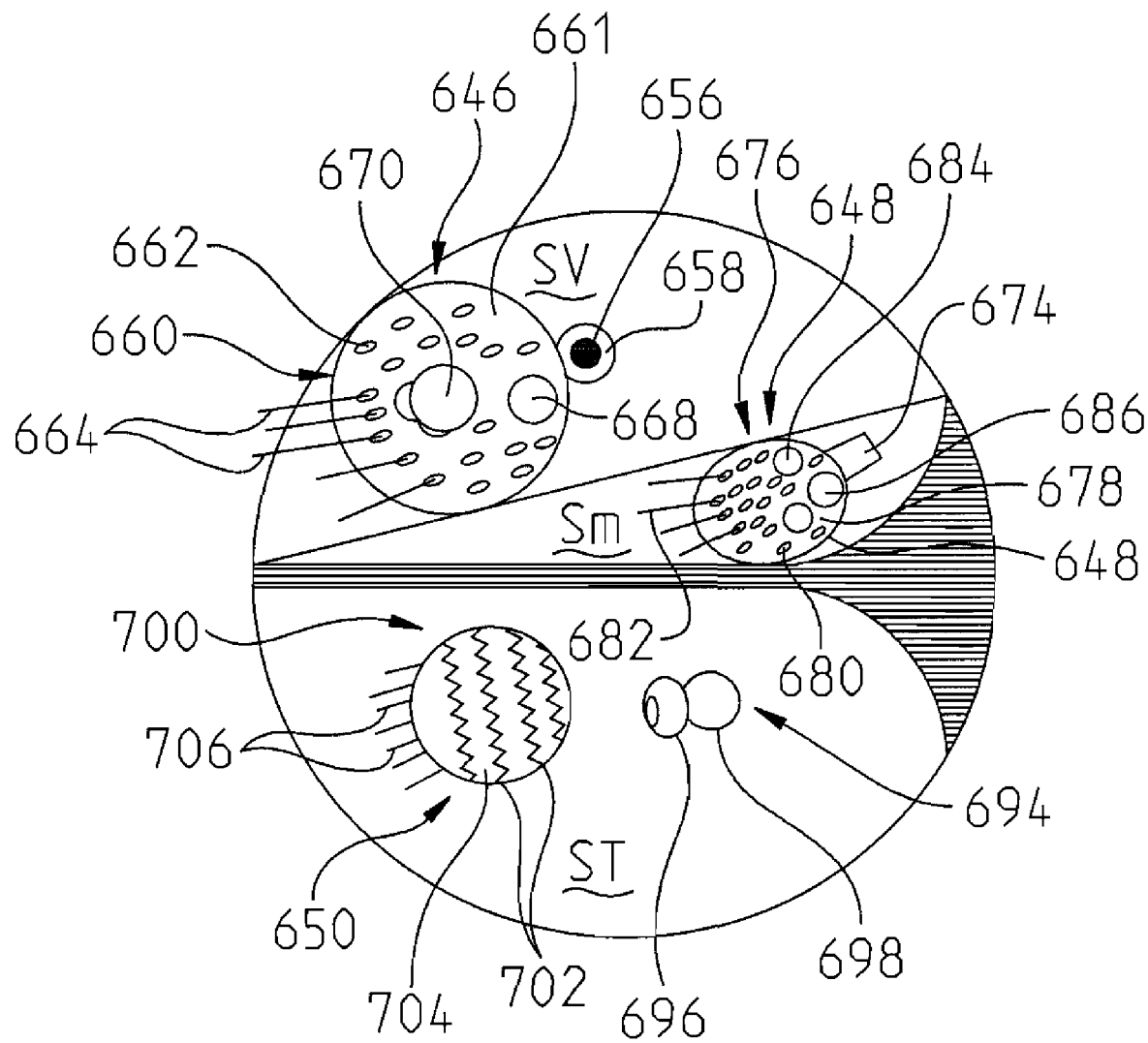

The reader's attention is now directed to FIGS. 8A, 8B and 8C, that illustrate different embodiments of the present invention inserted within the cochlea of a patient.

FIG. 8A shows a cross-sectional view of the cochlea, including the scala vestibuli SV, the scala media SM (also known as the cochlear duct), and the scala tympani ST. An implant 600 is shown inserted in the scala tympani ST that includes the spine portion 602 and an electrode containing portion 605. The spine 602 is shown as being encased within an insulating layer 604 to encase the spine 602, and to insulate it both electrically from the electrodes within the electrode portion, and chemically from the intra-cochlear fluids. The electrode containing portion 605 comprises a matrix that is comprised to a large extent of insulating material 606, with electrodes 610 extending through the insulating material 606. The insulating material 606 electrically insulates the electrodes 610 from each other. The electrodes extend toward the electrical distal brush ends 612 that extend radially outwardly from the implant 600 to place them in closer proximity to the modiolus. Formed within the electrode containing portion are inflow tubule 614 and outflow tubule 618.

It will be noted that distal brush ends 612 are shown as extending from only some of the electrodes 610. Actually, distal brush ends 612 will likely extend from all the electrodes 610. However, as the distal brush ends 612 are disposed along the length of the implant 600, not all of the electrodes will be viewable from the cross-sectional view of FIG. 8. The electrodes 610 that do not show the distal brush ends in the drawing would have their distal brush ends 612 extending radially outward at some other axial position along the implant 600.

Turning now to FIG. 8B, an implant 630 is shown. Implant 630 includes electrode-containing layers 634 that are formed into a "sandwich" and are sandwiched between insulating layers 636. Distal brush ends 638 extend radially outwardly from the main body of the electrode.

It is envisioned that the distal brush end 638 will emerge from the respective layers 634 at various places along the axial length of the electrode. It is also envisioned that the electrodes may emerge in "bunches", so that all of the electrodes contained within one of the particular layers will all emerge within the same general axial area. The electrode-containing portion 641 also includes inflow tubules 642 and outflow tubules 644, and may contain a large fluid containing reservoir tubule 640 for supplying the inflow tubule 642.

As best shown in FIG. 8C, a first implant 646 is shown as being inserted in the scala vestibuli SV, a second implant 648 is inserted within the scala media SM (or cochlear duct); and the third implant 650 is shown as being placed within the scala tympani ST. These three implants may be placed simultaneously into the three scala within one cross-sectional area of the cochlea, modiolus, and acoustic nerve.

The first implant 646 includes a spine 656 that is surrounded by an insulating layer 658. The spine 656 enables the implant to be given a curvature so as to hug the wall of the scala vestibuli SV. The implant 646 also includes an electrode-containing portion 660 that includes an insulating material in which the plurality of electrodes is embedded as they extend through the implant. The series of "ovals" shown in the implant designate electrodes 662 that extend through the insulating material.

It will be noted that some of the electrodes that extend through the implant include a distal brush end 664 that extends radially outwardly from the implant. Each of the electrodes is envisioned to have a distal brush end 664 that extends radially outwardly from the electrode bundle. However, at the particular cross-section taken in FIG. 8B, only some of the electrodes include distal brush end 664 extending radially outwardly therefrom, with the other electrodes extending radially outwardly therefrom at other axial locations of the implant 664. For example, some of the distal brush ends 664 may extend outwardly closer to the proximal end of the implant, whereas others may extend outwardly closer to the distal end of the implant. A plurality of inflow tubes 668 and outflow tubes 670 also extend through the insulating material 661 of the implant 646.

The second implant 648 is disposed in the scala media SM, and is generally similar to the first implant 646. The second implant 648 includes a spine 674 and an electrode-containing portion 676 that comprises an insulating material 678 through which a plurality of electrodes 680 extend. The electrodes have distal brush ends, such as distal brush end 682 that extend radially outwardly, along the length of the implant 648. The implant 648 also includes inflow tube 684 and outflow tube 686.

The third implant 650 is disposed in the scala tympani ST, and is slightly different from the first and second implant 646 and 648. The third implant 650 comprises a separate tube portion 694 that includes the inflow tube 696 and the outflow tube 698. The tube portions 694 is separated from and not a part of the implant 650, but preferably runs co-extensively with the length of the implant 650.

The electrode-containing portion 700 comprises a plurality of electrode layers 702 each of which includes a plurality of electrodes. The electrode layers 702 are sandwiched between insulating layers 704. The insulating layers 704, as with the insulating materials of the other two implants, are provided for electrically insulating the electrodes from each other, so that the signal and impulses being delivered by the electrodes do not intermingle. Distal brush ends 706 extend radially outwardly, from the electrode-containing portion 700, and comprise the distal ends of the electrodes. Preferably, the distal brush ends of the electrodes in each particular electrode layer emerge from the implant at about the same axial location along the implant.

The primary purpose of FIG. 8C is to illustrate that an implant system of the present invention may comprise multiple implants that are used within the cochlea, with different implants being placed in different portions of the cochlea. In some circumstances, it may be advisable to use implants of all the same type in each of the three chambers of the cochlea, whereas in other situations, it may be preferred to use one type of implant, such as the matrix implant, in the scala vestibuli SV, whereas another type of implant, such as the electrode layer implant 650, or solely a fluid tubule system 694 in another portion of the cochlea.

The insulation material, e.g. 704 may be a different material from the brush-ends e.g. 706 or the same material. The implants 605 (FIG. 8A), 646 (FIG. 8C) and 648 (FIG. 8C) organize the respective insulating materials 613, 661, 678 as a matrix of insulation with a cross-section showing a more dotted electrode and tubule pattern, as opposed to the layered, sheet-like organization of electrodes 634 (FIG. 8B), and 702 (FIG. 8C) of implants 630 (FIG. 8B), and 650 (FIG. 8C). When the insulation between the conductive fibers forms separate layers, it is seen as a "layered" or "sandwich" type (Implants 630 (FIG. 8C), 650 (FIG. 8C)). As shown in FIG. 5, certain areas of the implant 432 nanoelectrodes and tubules can be stimulated but with other areas being left unstimulated and acting as insulation.

The electrodes, tubules and spine materials are held together by adhesives or by a sheath that extends for distances along the implant. The sheath may have areas that are perforated or perforateable in order to allow for electrode and tubule exit from the implant body and allow for functioning electrode and tubule ends.

The top of the electrode sheath transition area 430 (FIG. 4B) between the implant 302 (FIG. 4) and the receiver-stimulator 313 (FIG. 4) might have a similar appearance to a printed circuit or ribbon-type wire bundle tape where one has a large number of electrical wire or printed paths, one for each group of brush like distal ends. Also, various brush-ends and their nanowires from various sites along the cochlea could be grouped together electrically. The nanotechnology containing intra-cochlear device structures may go out to the receiver-stimulator 313 and fluid control areas 314 directly, rather than having a "transition" area 430 close to the cochlea.

There are also several ways to get fluid to the fluid conduits of the implants. The embodiment shown in FIGS. 4A, 4B and 8-A, 8-C have several fluid conduits that serve a plurality of fluid tubules. One anticipated problem is that the very small diameters of the tubes may lead to the fluid tubules becoming clogged, thus preventing fluid from flowing to any of the distal ends of the fluid tubules. There may be some benefit to using a separate fluid conduit for each tubule, or possibly a separate fluid conduit for different sections of the electrode so that one might use, for example, five fluid conduits to serve, for example, 25 fluid tubules. In this way, each fluid conduit would serve one-fifth of the tubules.

Another embodiment has vacant areas between electrically conducting fibers that act as hollow channels to carry regenerative chemicals and cells into the cochlea and allow excess fluid to exit. Thus, the vacant areas devoid of nanofibers and wires would be the conduits and tubules for conducting fluid to and from the interior of the cochlea. Another embodiment, implant 650 has the tubule system 694 either attached to the exterior of the electrical components or separate from them altogether. This later type would facilitate removal of the tubule system from the cochlea if the tubule system needs to be replaced.

Rather than using a single intra-cochlear implant, it is useful in some situations to use multiple intra-cochlear implant electrodes. Thus, rather than one single electrode advancing the entire length of the cochlea, several electrodes would enter at several points progressively upwards on the cochlear spiral. The surgical position of one cochlear implant would be the lateral basal turn of the cochlea at the round window area. Secondary, tertiary and other sites for further electrode entry and function could include the middle turn in the lateral portion of the cochlea, the basal and middle turns in the middle cranial fossa, and the upper turn area on the lateral side of the cochlea.

Turning now to a multiple implant embodiment, one would desire to place one or more implant(s) at the basal turn, one or more implant(s) at the middle turn, and one or more implant(s) at the apical turn so that one could wire and stimulate, with electrical currents and chemical compounds, a greater number of tonotopic areas. As a generalization, the basal turn houses the highest frequencies; the middle turn, the middle frequencies; and the apical turn the lowest frequencies. Thus, by placing several electrodes in those areas, more nerve tissue in more tonotopic areas would be stimulated. The fluid tubule system would also be placed similarly.

FIG. 8C shows a multi-electrode array in a cross-section of the cochlea. It is important to remember when looking at this particular multi-electrode array that it is placing electrodes into three different cross-sectional cochlear anatomic areas. There may be one, two or three area electrodes with brush-ends, tubules and electrode studs that are all in the cochlea at one cross-sectional point along the length of the cochlea. These multi-electrode arrays within a cross-sectional cochlea area can be situated in the basal, middle and directly on the apical turns. So, this differs from the earlier discussion about the multi-implants where one electrode was in the basal turn, one in the middle turn and one in the apical turn. Thus, multiple implants can be placed in the cochlear duct (scala media SM), scala vestibuli, and/or scala tympani; alone or in any combination along the length of the cochlea.

The three different cross-sectional area electrode nano-brush-endings or tubules are directed at three different areas. Implant 648 (FIG. 8C), which is placed in the cochlear duct SM, can be used to encourage and stimulate nerve cells to grow into the osseous spiral lamina up into the previous area of the Organ of Corti. This is one way to have regeneration of actual Organ of Corti elements as well as stimulating them. The implant 646 placed in the scala vestibuli approaches the cochlear nerve and spiral ganglion in one region. However, with growth of new nerve endings, due to chemicals such as neurotrophins, it can give rise to whole new areas of neural tissue and allow further neuro-stimulation. Some of these new areas would not normally be present in nature as the nerves and structures regenerate through and into the scala vestibuli where they normally would not be found. New regenerated otologic anatomy could be found in otologic areas, such as the scala tympani, scala vestibui, scala media, modiolus, and acoustic nerve, not normally containing the new, regenerated anatomy.

In the scala tympani modiolar area, one would find nerve-type cells. Normally, the remaining nerve and spiral ganglion cells stimulated by an implant 650 are found closest to the scala tympani. So therefore, the scala tympani is the place in which one would conventionally insert an intra-cochlear implant. However, as in the scala vestibuli electrode discussion, nerve tissue may also grow to touch the scala tympani electrode by anatomically regenerated structures not normally found in this area.

Normally, the nerve cells are present from the cochlear nerve to the spiral ganglion area, up into the osseous spiral lamina, and then into the Organ of Corti. The Corti's Organ sits within the cochlear duct SM. Since the cochlear duct contents have degenerated in deaf patients, the nerve cells will degenerate retrograde towards the spiral ganglion area. Using regenerative techniques, new anatomic growth will occur into the scala media so that new neural tissue, cells, and organs can be found in the cochlear duct area and can be stimulated.

Within the scala tympani, the spiral ganglion is covered with a thin sheet of porous bone, so one is stimulating through the bone. With stimulation by regenerative substances, the nerve cells can foster the growth of dendrites through the porous bone, and into the fluid space of the scala tympani ST. With the scala vestibuli SV electrode components, the same thing can happen. With perfusion or substance stimulation, the spiral ganglion would grow and send some of its fibers up into the scala vestibuli. The same would happen for the cochlea duct SM. In other words, the scala tympani, the scala vestibuli, plus the cochlear duct are available for stimulation by the electrode. The more nerve elements that are stimulated, the better the sound reproduction.

"Electrical-acoustical stimulation" hearing enhancement uses an ordinary hearing aid for low-to-mid frequencies along with an implanted scala tympani device for mid-to-high frequencies. The overall hearing aid device that the person would possess and use would be a device employing both acoustical and electrical stimulation. "Electrical-acoustical stimulation" is in the prior art, but does not contain the marked advantages of the novel nanotechnology electrodes or fluid delivery systems described in this application. Nano brush-end stimulation can approximate naturally occurring numbers of hearing receptor cells stimulating the hearing nerve endings. The fluid delivery system can allow for growth and regeneration of new nerve elements and hearing organs to replace or augment empty, residual, or damaged anatomy.

In another embodiment, the electrode with the brush-ends and tubules could be used in combination with acoustical stimulation. In some hearing loss patient cases, only the high frequencies have been lost to hearing. Therefore, the upper portions of the cochlea are still intact and hearing normally. The advantage of using an intra-cochlear electrode with brush-ends and tubules is that the actual high frequency internal cochlear anatomy would be stimulated in many more points and regeneration of structures would occur. The implant doesn't directly involve the normal hearing, lower frequency, non-hearing loss areas. However, by acting on the non-functional high frequency basal turn structures, it compliments the intact middle and upper turn hearing structures. The electrode would be placed in the basal turn of the cochlea since the hearing structures are functioning at good capacity in the middle and apical cochlear turns.

One of the problems with intra-cochlear implants is that if you insert an intra-cochlear implant partially into the cochlea at the basal turn area, where the high frequencies are to be stimulated, the partial insertion of the intra-cochlear implant can result in a total hearing loss. By contrast, in the present invention, the small fluid-containing tubules would extend from the electrode into the cochlear fluid spaces and introduce chemicals, compounds, molecules and/or cells into, thus fostering regeneration of hearing anatomy and function. The differentation would be that if someone has good low tone hearing (apical turn) and is deaf in the higher frequencies (basal turn), one may, for example, put an electrode array only on the basal turn of the cochlea, or just confine it to the basal and middle turn areas, or place one in the basal, the other in the middle turns.

Additionally, access can be gained to the cochlea in the basal and middle turns of the middle cranial fossa approach. The middle cranial fossa approach is well described in the literature with regard to access of the internal auditory canal and placement of intra-cochlear implants. When using the middle fossa approach for an implant, surgery would prepare an area of endosteum in the basal and/or middle turns, followed by placement of an electrode 401, 432 (FIGS. 4A, B) with its sheath transition area 430, (FIG. 4B), and would then be covered with a protective fascia graft.

The apical turn approach is different from either of the basal or middle turn approaches just discussed. As the apical turn is very small, a smaller set of electrodes is placed within the cochlea in order to fit properly. In this case, the tensor tympani muscle would be removed. This would allow drilling through the cochlear bone with eventual exposure of the middle and apical cochlear turns.

Having described the invention in detail with reference to certain preferred embodiments, it will be appreciated that variations and modifications exist and would be understood to a person having ordinary skill in the art. It is also understood that the invention described herein is to be limited only by the scope and spirit of the appended claims.

What is claimed is:

1. For implantation into a an interior chamber of a mammalian cochlea having a wall defining the interior chamber, an intra-cochlear implant for aiding in the hearing of a patient, the implant comprising a body portion implantable within an interior chamber of a cochlea of a patient, the body portion having a proximal end, and a distal end, and a primary axis, a plurality of signal carrying electrodes extending along the body portion for carrying a plurality of different signals, the electrodes having proximal ends and distal ends, the proximal ends being capable of receiving a plurality of different signals from a signal generator, and the distal ends being capable of delivering the received plurality of different signals to a plurality of anatomical receptors within a cochlea, wherein at least several of the plurality of electrodes have a nano-electrode sized portion and wherein the distal ends of the plurality of electrodes are configured not to become connected to the wall defining the interior chamber.

2. The implant of claim 1 wherein the nano-electrode sized portion comprises substantially the entire length of the several electrodes.

3. The implant of claim 1 wherein the body portion comprises a bundle of the plurality of electrodes, wherein the electrodes comprise electrodes having different lengths.

4. The implant of claim 1 wherein the several electrodes include electrodes having portions extending through cochlear cavity fluids, said portions having a radially extending distal portion for positioning the distal end of the electrodes proximate to a wall of a cochlea.

5. The implant of claim 4 wherein the distal portions have a sufficient radial extent to position their distal ends in contact with a wall of the cochlea.

6. The implant of claim 4 wherein the electrodes having radially extending distal portions have distal portions of varying radial extent to place the distal ends of the distal portions at varying distances from a wall of a cochlea.

7. The implant of claim 1 further comprising a slow release compound containing a pharmacologically active agent.

8. The implant of claim 7 further comprising a fluid delivery tubule disposed at least partially within an interior of a cochlea, wherein the slow release compound is coupled to at least one of the electrodes and fluid delivery tubules.

9. The implant of claim 8 wherein the slow release compound is capable of at least one of reducing debris build-up on the implant and reducing blockage in the fluid delivery tubule.

10. The implant of claim 7 wherein the pharmacologically active agent is selected from the group consisting of neurotrophins, antioxidants, medications, growth stimulants, stem cells, vasoactive compounds, nucleotides, RNA, DNA, nutrients, cells, nano-robots, antibiotics, antifungals, hormones, anti-seizure medicines, growth hormones and libido enhancement compounds.

11. The implant of claim 1 wherein the body portion includes an insulating material for electrically insulating the electrodes.

12. The implant of claim 11 wherein the insulating material is disposed between the electrodes for electrically insulating the electrodes from each other.

13. The implant of claim 11 wherein the insulating material is disposed in layers in the body portion and the electrodes are disposed in layers in the body portion.

14. The implant of claim 13 wherein the layers of insulating materials are disposed between the layers of electrodes to electrically insulate the layers of electrodes.

15. The implant of claim 1 further comprising a fluid outflow tubule having a distal end for being disposed within an interior of a cochlea and a proximal end, the outflow tubule being capable of receiving fluid from an interior of a cochlea and delivering the fluid to an exterior of a cochlea.

16. The implant of claim 1 wherein the several electrodes having a nano-electrode sized portion comprise at least about fifty electrodes having nano-electrical sized portion.

17. The implant of claim 1 wherein the body portion includes a sheath disposed exteriorly around at least a portion of the body portion.

18. The implant of claim 1 wherein the proximal ends of the signal carrying electrode are electrically coupled to a signal generator.

19. The implant of claim 1 wherein the body portion includes a spine member formable to import a curvilinear axis to the body portion, the spine member being comprised of a titanium-nickel shape memory alloy.

20. The implant of claim 1 wherein the nano-electrode sized portion comprises at least one of a single wall nanotubule electrode and a multi-wall nanotubule electrode.

21. The implant of claim 1 wherein the body portion includes a spine portion formed from a plurality of nano-electrode sized members formed into a non-linear shape to impart a non-linear shape to the implant.

22. The implant of claim 1 wherein the implant includes a light signal carrying member capable of carrying a light signal to an interior of a cochlea for performing at least one of stimulating growth of anatomical structures in a cochlea, and stimulating nerve endings in an ear to send a signal to a brain.

23. An intra-cochlear implant for aiding in the hearing of a patient, comprising a body portion implantable within an interior of a cochlea of a patient, the body portion having a proximal end, and a distal end, and a primary axis, a plurality of signal carrying electrodes extending along the body portion for carrying a plurality of different signals, the plurality of electrodes having proximal ends and distal ends, the proximal ends being capable of receiving a plurality of signals from a signal generator, and the distal ends being capable of delivering the received plurality of signals to a plurality of anatomical receptors within a cochlea, wherein at least several of the plurality of signal carrying electrodes have a nano-electrode sized portion, and a fluid delivery tubule having a proximal end and a distal end, the distal end being disposed within an interior chamber of a cochlea.

24. The implant of claim 23 wherein the fluid delivery tubule is coupled to the body portion, and includes an inflow portion and an outflow portion, the inflow portion having a proximal end capable of receiving fluid from a fluid source, and the distal end is capable of delivering the received fluid to the interior of the cochlea; the outflow portion having a distal end capable of being disposed within an interior of a cochlea and a proximal end, the outflow portion being capable of receiving fluid from an interior of a cochlea and delivering the fluid to an exterior of a cochlea.

25. The implant of claim 24 further comprising a fluid outflow tubule having a distal end for being disposed within an interior of a cochlea, and a proximal end, the distal end being capable of receiving a fluid from an interior of a cochlea, and the proximal end being capable of delivering the received fluid to an exterior of a cochlea.

26. The implant of claim 23 wherein the fluid delivery tubule includes an outflow portion having a distal end capable of being disposed within an interior of a cochlea and a proximal end, the outflow portion being capable of receiving fluid from an interior of a cochlea and delivering the fluid to an exterior of a cochlea.

27. For implantation into an interior chamber of a mammalian cochlea having a wall defining the interior chamber, an intra-cochlear implant for aiding in the hearing of a patient, the implant comprising a body portion implantable within an interior chamber of a cochlea of a patient, the body portion having a proximal end, and a distal end, and a primary axis, a plurality of signal carrying electrodes extending along the body portion, the electrodes having proximal ends and distal ends, the proximal ends being capable of receiving a signal from a signal generator, and the distal ends being capable of delivering the received signal to an anatomical receptor within a cochlea, wherein at least several of the plurality electrodes have a nano-electrode sized portion and wherein the distal ends of the plurality of electrodes are configured not to become connected to the wall defining the interior chamber, further comprising a buckey ball including a slow release compound containing a pharmacologically active agent.

28. An intra-cochlear implant for aiding in the hearing of a patient, comprising a body portion implantable within an interior of a cochlea of a patient, the body portion having a proximal end, and a distal end, and a primary axis and wherein the body portion includes a first body portion placeable in a first chamber of a cochlea, and a second body portion placeable in a second chamber of a cochlea, a plurality of signal carrying electrodes for carrying a plurality of different signals extending along the body portion, the plurality of signal carrying electrodes having proximal ends and distal ends, the proximal ends being capable of receiving a plurality of different signals from a signal generator, and the distal ends being capable of delivering the plurality of different signals received from the signal generator to a plurality of anatomical receptors within a cochlea, wherein at least several of the plurality electrodes have a nano-electrode sized portion.

29. The implant of claim 28 wherein the body portion further includes a third body portion placeable in a third chamber of a cochlea.

30. An intra-cochlear implant for aiding in the hearing of a patient, comprising a body portion implantable within an interior of a cochlea of a patient, a plurality of signal carrying electrodes capable of receiving a signal from a signal generator and delivering the received signal to an anatomical receptor within a cochlea, wherein at least several of the plurality electrodes have a nano-electrode sized portion; and a fluid delivery tubule including an inflow portion and an outflow portion, the inflow portion having a proximal end and a distal end, the proximal end being capable of receiving a fluid from a fluid source, and the distal end, being disposed within an interior of the cochlea, and being capable of delivering the received fluid to the interior of the cochlea; and the outflow portion having a distal end capable of being disposed within an interior of a cochlea and a proximal end, the outflow portion being capable of receiving fluid from an interior of a cochlea and delivering the fluid to an exterior of a cochlea.

31. The implant of claim 30 further comprising a reservoir for storing a fluid for delivery to an interior of a cochlea, the reservoir being disposed internally within a patient and in fluid communication with the fluid delivery tubule.

32. The implant of claim 31 further comprising a subcutaneously disposed osmotic pump for pumping fluid from the reservoir to the fluid delivery tubule.

33. The implant of claim 30 wherein the fluid delivery tubule includes a distal portion disposed adjacent the distal end, the distal portion including a radially extending portion for placing the distal end in proximity to a wall of a cochlea.

34. The implant of claim 30 wherein the fluid delivery tubule includes at least a first and a second branch for delivering fluid to a first and a second portion of the cochlea.

35. The implant of claim 34 wherein the first branch of the fluid delivery tubule includes a radially extending distal portion for placing a distal end of the branch adjacent to a wall of the cochlea.

36. The implant of claim 30 wherein the fluid delivery tubule includes a juncture portion for coupling the inflow portion to the outflow portion.

37. The implant of claim 30 wherein the fluid from the fluid source is selected from the group consisting of neurotrophins, antioxidants, medications, growth stimulants, stem cells, vasoactive compounds, nucleotides, RNA, DNA, nutrients, cells, nano-robots, antibiotics, antifungals, hormones, anti-seizure medicines, growth hormones and libido enhancement compounds.

38. The implant of claim 30 wherein the fluid delivery tubule includes an interior diameter large enough to permit the passage of cellular material therethrough.

39. The implant of claim 30 wherein the fluid delivery tubule is capable of carrying an electrical signal, and is capable of delivering the carried electrical signal to an anatomical receptor within a cochlea.

40. An intra-cochlear implant for aiding in the hearing of a patient, comprising a body portion implantable within an interior of a cochlea of a patient, a plurality of signal carrying electrodes capable of receiving a signal from a signal generator and delivering the received signal to an anatomical receptor within a cochlea; and a fluid delivery tubule including an inflow portion and an outflow portion, and a juncture portion for coupling the inflow portion to the outflow portion the inflow portion having a proximal end and a distal end, the proximal end being capable of receiving a fluid from a fluid source, and the distal end, being disposed within an interior of the cochlea, and being capable of delivering the received fluid to the interior of the cochlea; and the outflow portion having a distal end capable of being disposed within an interior of a cochlea and a proximal end, the outflow portion being capable of receiving fluid from an interior of a cochlea and delivering the fluid to an exterior of a cochlea, wherein the fluid delivery tubule includes an interior passageway through which fluid can flow, the inflow portion includes at least one delivery aperture for placing the interior passageway in fluid communication with an interior of a cochlea through which fluid can flow from the passageway to an interior of a cochlea, and the outflow portion includes at least one uptake aperture for placing the interior passageway in fluid communication with an interior of a cochlea through which fluid can flow from an interior of a cochlea into the interior passageway.

41. An intra-cochlear implant for aiding in the hearing of a patient, comprising a body portion implantable within an interior of a cochlea of a patient, a plurality of signal carrying electrodes capable of receiving a signal from a signal generator and delivering the received signal to an anatomical receptor within a cochlea; and a fluid delivery tubule including an inflow portion and an outflow portion, the inflow portion having a proximal end and a distal end, the proximal end being capable of receiving a fluid from a fluid source, and the distal end, being disposed within an interior of the cochlea, and being capable of delivering the received fluid to the interior of the cochlea; and the outflow portion having a distal end capable of being disposed within an interior of a cochlea and a proximal end, the outflow portion being capable of receiving fluid from an interior of a cochlea and delivering the fluid to an exterior of a cochlea, wherein the fluid from the fluid source comprises a pharmacological agent capable of stimulating the growth of at least one of an anatomical structures and tissue in an interior of the cochlea.

* * * * *